(12) United States Patent
Wolfe

(10) Patent No.: US 12,342,988 B2
(45) Date of Patent: *Jul. 1, 2025

(54) DISPOSABLE AIR/WATER AND SUCTION VALVES FOR AN ENDOSCOPE

(71) Applicant: EndoChoice, Inc., Alpharetta, GA (US)

(72) Inventor: Justin Wolfe, Lawrenceville, GA (US)

(73) Assignee: EndoChoice, Inc., Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/656,720

(22) Filed: Mar. 28, 2022

(65) Prior Publication Data
US 2022/0211256 A1    Jul. 7, 2022

Related U.S. Application Data

(63) Continuation of application No. 16/680,025, filed on Nov. 11, 2019, now Pat. No. 11,311,181, which is a
(Continued)

(51) Int. Cl.
*A61B 1/00* (2006.01)
*A61B 1/015* (2006.01)

(52) U.S. Cl.
CPC .......... *A61B 1/015* (2013.01); *A61B 1/00068* (2013.01); *A61B 1/00094* (2013.01); *A61B 1/00103* (2013.01); *A61B 1/00137* (2013.01)

(58) Field of Classification Search
CPC . A61B 1/015; A61B 1/00068; A61B 1/00094; A61B 1/00103; A61B 1/00137
See application file for complete search history.

(56) References Cited

U.S. PATENT DOCUMENTS

| | | |
|---|---|---|
| 3,639,714 A | 2/1972 | Fujimoto |
| 3,955,064 A | 5/1976 | Demetrio |
| (Continued) | | |

FOREIGN PATENT DOCUMENTS

| | | |
|---|---|---|
| CA | 2297986 | 3/1999 |
| CA | 2765559 | 12/2010 |
| (Continued) | | |

OTHER PUBLICATIONS

Notice of Allowance dated Apr. 12, 2017 for U.S. Appl. No. 14/603,137.
(Continued)

*Primary Examiner* — Anh Tuan T Nguyen
*Assistant Examiner* — Rynae E Boler
(74) *Attorney, Agent, or Firm* — Seager, Tufte & Wickhem, LLP

(57) ABSTRACT

A disposable air/water valve for an endoscope, including a shaft having a passage from an opening to a vent. The shaft has grooves and ridges and a protrusion formed at the vent. Seals are set within some of the grooves. An inner ring, having a diaphragm, extends from an outer circumference of the inner ring to an internal circumference of an outer cap. Hinges extend vertically downward from the diaphragm and ribs are formed along the internal circumference of the outer cap. A button cap has an internal ring that securely attaches to the shaft. A resilient member is securely disposed between the button cap and the diaphragm. The outer cap, inner ring, and internal ring of the button cap define a central bore to accommodate the shaft therein.

19 Claims, 25 Drawing Sheets

Related U.S. Application Data continuation of application No. 15/355,390, filed on Nov. 18, 2016, now Pat. No. 10,898,062.

(60) Provisional application No. 62/375,359, filed on Aug. 15, 2016, provisional application No. 62/259,573, filed on Nov. 24, 2015.

(56) References Cited

U.S. PATENT DOCUMENTS

| | | |
|---|---|---|
| 4,027,697 A | 6/1977 | Bonney |
| 4,037,588 A | 7/1977 | Heckele |
| 4,084,401 A | 4/1978 | Belardi |
| 4,361,138 A | 11/1982 | Kinoshita |
| 4,402,313 A | 9/1983 | Yabe |
| 4,461,282 A | 7/1984 | Ouchi |
| 4,494,549 A | 1/1985 | Namba |
| 4,532,918 A | 8/1985 | Wheeler |
| 4,588,294 A | 5/1986 | Siegmund |
| 4,641,635 A | 2/1987 | Yabe |
| 4,694,821 A | 9/1987 | Kondo |
| 4,727,859 A | 3/1988 | Lia |
| 4,736,732 A | 4/1988 | Shimonaka et al. |
| 4,764,001 A | 8/1988 | Yokota |
| 4,801,792 A | 1/1989 | Yamasita |
| 4,825,850 A | 5/1989 | Opie |
| 4,877,314 A | 10/1989 | Kanamori |
| 4,902,115 A | 2/1990 | Takahashi |
| 4,976,522 A | 12/1990 | Igarashi |
| 4,984,878 A | 1/1991 | Miyano |
| 5,007,406 A | 4/1991 | Takahashi |
| 5,014,685 A | 5/1991 | Takahashi |
| 5,193,525 A | 3/1993 | Silverstein |
| 5,224,929 A | 7/1993 | Remiszewski |
| 5,296,971 A | 3/1994 | Mori |
| 5,359,456 A | 10/1994 | Kikuchi |
| 5,395,329 A | 3/1995 | Fleischhacker |
| 5,447,148 A | 9/1995 | Oneda |
| 5,460,167 A | 10/1995 | Yabe |
| 5,464,007 A | 11/1995 | Krauter |
| 5,475,420 A | 12/1995 | Buchin |
| 5,489,256 A | 2/1996 | Adair |
| 5,518,501 A | 5/1996 | Oneda |
| 5,518,502 A | 5/1996 | Kaplan |
| 5,547,455 A | 8/1996 | Mckenna |
| 5,547,457 A | 8/1996 | Tsuyuki |
| 5,575,755 A | 11/1996 | Krauter |
| 5,587,839 A | 12/1996 | Miyano |
| 5,630,782 A | 5/1997 | Adair |
| 5,630,798 A | 5/1997 | Beiser |
| 5,662,588 A | 9/1997 | Iida |
| 5,674,182 A | 10/1997 | Suzuki |
| 5,685,821 A | 11/1997 | Pike |
| 5,685,823 A | 11/1997 | Ito |
| 5,702,347 A | 12/1997 | Yabe |
| 5,707,344 A | 1/1998 | Nakazawa |
| 5,725,474 A | 3/1998 | Yasui |
| 5,725,476 A | 3/1998 | Yasui |
| 5,725,477 A | 3/1998 | Yasui |
| 5,725,478 A | 3/1998 | Saad |
| 5,777,797 A | 7/1998 | Miyano |
| 5,782,751 A | 7/1998 | Matsuno |
| 5,800,341 A | 9/1998 | Mckenna |
| 5,810,715 A | 9/1998 | Moriyama |
| 5,810,717 A | 9/1998 | Maeda |
| 5,810,770 A | 9/1998 | Chin |
| 5,830,121 A | 11/1998 | Enomoto |
| 5,836,894 A | 11/1998 | Sarvazyan |
| 5,840,015 A * | 11/1998 | Ogino .............. A61M 1/7413 600/156 |
| 5,860,913 A | 1/1999 | Yamaya |
| 5,870,234 A | 2/1999 | EbbesmeierneeSchitthof |
| 5,871,441 A * | 2/1999 | Ishiguro .............. A61B 1/122 600/159 |
| 5,916,148 A | 6/1999 | Tsuyuki |
| 5,940,126 A | 8/1999 | Kimura |
| 6,058,109 A | 5/2000 | Lechleider |
| 6,095,970 A | 8/2000 | Hidaka |
| 6,095,971 A | 8/2000 | Takahashi |
| 6,117,068 A | 9/2000 | Gourley |
| 6,181,481 B1 | 1/2001 | Yamamoto |
| 6,196,967 B1 | 3/2001 | Lim |
| 6,261,226 B1 | 7/2001 | Mckenna |
| 6,277,064 B1 | 8/2001 | Yoon |
| 6,346,075 B1 * | 2/2002 | Arai .............. A61B 1/00068 600/159 |
| 6,359,674 B1 | 3/2002 | Horiuchi |
| 6,375,610 B2 | 4/2002 | Verschuur |
| 6,402,738 B1 | 6/2002 | Ouchi |
| 6,419,626 B1 | 7/2002 | Yoon |
| 6,476,851 B1 | 11/2002 | Nakamura |
| 6,520,908 B1 | 2/2003 | Ikeda |
| 6,636,254 B1 | 10/2003 | Onishi |
| 6,638,214 B2 | 10/2003 | Akiba |
| 6,673,012 B2 | 1/2004 | Fujii |
| 6,690,337 B1 | 2/2004 | MayerIII |
| 6,712,760 B2 | 3/2004 | Sano |
| 6,832,984 B2 | 12/2004 | Stelzer |
| 6,888,119 B2 | 5/2005 | Iizuka |
| 6,908,429 B2 | 6/2005 | Heimberger |
| 6,997,871 B2 | 2/2006 | Sonnenschein |
| 7,154,378 B1 | 12/2006 | Ertas |
| 7,435,218 B2 | 10/2008 | Krattiger |
| 7,621,869 B2 | 11/2009 | Ratnakar |
| 7,630,148 B1 | 12/2009 | Yang |
| 7,701,650 B2 | 4/2010 | Lin |
| 7,713,246 B2 | 5/2010 | Shia |
| 7,746,572 B2 | 6/2010 | Asami |
| 7,813,047 B2 | 10/2010 | Wang |
| 7,828,725 B2 | 11/2010 | Maruyama |
| 7,918,788 B2 | 4/2011 | Lin |
| 7,927,272 B2 | 4/2011 | Bayer |
| 7,967,745 B2 | 6/2011 | Gilad |
| 7,976,462 B2 | 7/2011 | Wright |
| 8,064,666 B2 | 11/2011 | Bayer |
| 8,182,422 B2 | 5/2012 | Bayer |
| 8,197,399 B2 | 6/2012 | Bayer |
| 8,235,887 B2 | 8/2012 | Bayer |
| 8,262,558 B2 | 9/2012 | Sato |
| 8,287,446 B2 | 10/2012 | Bayer |
| 8,289,381 B2 | 10/2012 | Bayer |
| 8,300,325 B2 | 10/2012 | Katahira |
| 8,310,530 B2 | 11/2012 | Bayer |
| 8,353,860 B2 | 1/2013 | Boulais |
| 8,447,132 B1 | 5/2013 | Galil |
| 8,449,457 B2 | 5/2013 | Aizenfeld |
| 8,460,182 B2 | 6/2013 | Ouyang |
| 8,585,584 B2 | 11/2013 | Ratnakar |
| 8,587,645 B2 | 11/2013 | Bayer |
| 8,672,836 B2 | 3/2014 | Higgins |
| 8,715,168 B2 | 5/2014 | Ratnakar |
| 8,797,392 B2 | 8/2014 | Bayer |
| 8,872,906 B2 | 10/2014 | Bayer |
| 8,926,502 B2 | 1/2015 | Levy |
| 9,044,185 B2 | 6/2015 | Bayer |
| 9,101,266 B2 | 8/2015 | Levi |
| 9,101,268 B2 | 8/2015 | Levy |
| 9,101,287 B2 | 8/2015 | Levy |
| 9,144,664 B2 | 9/2015 | Jacobsen |
| 9,161,680 B2 | 10/2015 | Bellofatto et al. |
| 9,289,110 B2 | 3/2016 | Woolford |
| 9,307,890 B2 | 4/2016 | Ouchi |
| 9,314,147 B2 | 4/2016 | Levy |
| 9,320,419 B2 | 4/2016 | Kirma |
| 9,408,523 B2 | 8/2016 | Grudo et al. |
| 9,585,545 B2 | 3/2017 | Anderson et al. |
| 9,603,509 B2 | 3/2017 | Ando |
| 9,642,512 B2 | 5/2017 | Toyoda |
| 2001/0036322 A1 | 11/2001 | Bloomfield |
| 2002/0017515 A1 | 2/2002 | Obata |
| 2002/0047897 A1 | 4/2002 | Sugimoto |
| 2002/0087047 A1 | 7/2002 | Remijan |
| 2002/0109771 A1 | 8/2002 | Ledbetter |
| 2002/0109774 A1 | 8/2002 | Meron |

(56) References Cited

U.S. PATENT DOCUMENTS

| | | |
|---|---|---|
| 2002/0161279 A1 | 10/2002 | Luloh |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |
| 2003/0083552 A1 | 5/2003 | Remijan |
| 2003/0128893 A1 | 7/2003 | Castorina |
| 2003/0139650 A1 | 7/2003 | Homma |
| 2003/0153897 A1 | 8/2003 | Russo |
| 2003/0158503 A1 | 8/2003 | Matsumoto |
| 2003/0163029 A1 | 8/2003 | Sonnenschein |
| 2003/0181786 A1 | 9/2003 | Heimberger |
| 2004/0015054 A1 | 1/2004 | Hino |
| 2004/0046865 A1 | 3/2004 | Ueno |
| 2004/0061780 A1 | 4/2004 | Huffman |
| 2004/0064019 A1 | 4/2004 | Chang |
| 2004/0077927 A1 | 4/2004 | Ouchi |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2004/0260151 A1 | 12/2004 | Akiba |
| 2005/0018042 A1 | 1/2005 | Rovegno |
| 2005/0020876 A1 | 1/2005 | Shioda |
| 2005/0038317 A1 | 2/2005 | Ratnakar |
| 2005/0047134 A1 | 3/2005 | Mueller |
| 2005/0057687 A1 | 3/2005 | Irani |
| 2005/0090709 A1 | 4/2005 | Okada |
| 2005/0096501 A1 | 5/2005 | Stelzer |
| 2005/0119527 A1 | 6/2005 | Banik |
| 2005/0124858 A1 | 6/2005 | Matsuzawa |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0277808 A1 | 12/2005 | Sonnenschein |
| 2005/0283048 A1 | 12/2005 | Gill |
| 2006/0004257 A1 | 1/2006 | Gilad |
| 2006/0041190 A1 | 2/2006 | Sato |
| 2006/0047184 A1 | 3/2006 | Banik |
| 2006/0063976 A1 | 3/2006 | Aizenfeld |
| 2006/0069314 A1 | 3/2006 | Farr |
| 2006/0111613 A1 | 5/2006 | Boutillette |
| 2006/0114986 A1 | 6/2006 | Knapp |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0235306 A1 | 10/2006 | Cotter |
| 2006/0252994 A1 | 11/2006 | Ratnakar |
| 2006/0264704 A1 | 11/2006 | Fujimori |
| 2006/0293556 A1 | 12/2006 | Garner |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | Mccutcheon |
| 2007/0206945 A1 | 9/2007 | Delorme |
| 2007/0213591 A1 | 9/2007 | Aizenfeld |
| 2007/0229656 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0265492 A1 | 11/2007 | Sonnenschein |
| 2007/0270642 A1 | 11/2007 | Bayer |
| 2007/0279486 A1 | 12/2007 | Bayer |
| 2007/0286764 A1 | 12/2007 | Noguchi |
| 2007/0293720 A1 | 12/2007 | Bayer |
| 2008/0009673 A1 | 1/2008 | Khachi |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0091065 A1 | 4/2008 | Oshima |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 7/2008 | Courtney |
| 2008/0246771 A1 | 10/2008 | ONeal |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0076327 A1 | 3/2009 | Ohki |
| 2009/0082624 A1 | 3/2009 | Joko |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0213211 A1 | 8/2009 | Bayer |
| 2009/0216084 A1 | 8/2009 | Yamane |
| 2009/0225159 A1 | 9/2009 | Schneider |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0280322 A1 | 11/2010 | Mizuyoshi |
| 2010/0296178 A1 | 11/2010 | Genet |
| 2010/0326703 A1 | 12/2010 | Gilad |
| 2011/0004058 A1 | 1/2011 | Oneda |

(56) References Cited

U.S. PATENT DOCUMENTS

| | | |
|---|---|---|
| 2011/0004059 A1 | 1/2011 | Arneson |
| 2011/0034769 A1 | 2/2011 | Adair |
| 2011/0063427 A1 | 3/2011 | Fengler |
| 2011/0084835 A1 | 4/2011 | Whitehouse |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takato |
| 2011/0254937 A1 | 10/2011 | Yoshino |
| 2011/0263938 A1 | 10/2011 | Levy |
| 2011/0282144 A1 | 11/2011 | Gettman |
| 2011/0292258 A1 | 12/2011 | Adler |
| 2012/0040305 A1 | 2/2012 | Karazivan |
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0162402 A1 | 6/2012 | Amano |
| 2012/0200683 A1 | 8/2012 | Oshima |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |
| 2012/0253121 A1 | 10/2012 | Kitano |
| 2012/0277535 A1 | 11/2012 | Hoshino |
| 2012/0281536 A1 | 11/2012 | Gell |
| 2012/0289858 A1 | 11/2012 | Ouyang |
| 2012/0300999 A1 | 11/2012 | Bayer |
| 2013/0053646 A1 | 2/2013 | Yamamoto |
| 2013/0057724 A1 | 3/2013 | Miyahara |
| 2013/0060086 A1 | 3/2013 | Talbert |
| 2013/0066297 A1 | 3/2013 | Shtul |
| 2013/0077257 A1 | 3/2013 | Tsai |
| 2013/0085329 A1 | 4/2013 | Morrissette |
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0141557 A1 | 6/2013 | Kawata |
| 2013/0150671 A1 | 6/2013 | Levy |
| 2013/0158344 A1 | 6/2013 | Taniguchi |
| 2013/0169843 A1 | 7/2013 | Ono |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0222640 A1 | 8/2013 | Baek |
| 2013/0253268 A1 | 9/2013 | Okada |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303844 A1* | 11/2013 | Grudo ............... A61B 1/00105 600/101 |
| 2013/0303979 A1 | 11/2013 | Stieglitz |
| 2013/0317295 A1 | 11/2013 | Morse |
| 2013/0338442 A1* | 12/2013 | Anderson ............ A61B 1/015 600/154 |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0148644 A1 | 5/2014 | Levi |
| 2014/0184766 A1 | 7/2014 | Amling |
| 2014/0213850 A1 | 7/2014 | Levy |
| 2014/0225998 A1 | 8/2014 | Dai |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0298932 A1 | 10/2014 | Okamoto |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0144215 A1 | 5/2015 | Bellofatto et al. |
| 2015/0148608 A1* | 5/2015 | Fukushima ........ A61B 1/00094 600/116 |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| EP | 0055394 B1 | 3/1985 |
| EP | 0998212 B1 | 4/2002 |
| EP | 1690497 | 8/2006 |
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |

(56) References Cited

FOREIGN PATENT DOCUMENTS

| | | |
|---|---|---|
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | H08112250 | 5/1996 |
| JP | H1043129 | 2/1998 |
| JP | H10239740 | 9/1998 |
| JP | 11137512 | 5/1999 |
| JP | 2000217777 | 8/2000 |
| JP | 2003/305003 A | 10/2003 |
| JP | 2003310542 A * | 11/2003 |
| JP | 2005253543 | 9/2005 |
| JP | 2006025888 | 2/2006 |
| JP | 2006068109 | 3/2006 |
| JP | 2006175175 | 7/2006 |
| JP | 2007111266 | 5/2007 |
| JP | 2010178766 A | 8/2010 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014510547 | 5/2014 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 A1 | 12/2010 |
| WO | 2012038958 | 3/2012 |
| WO | 2012056453 A2 | 5/2012 |
| WO | 2012075153 A2 | 6/2012 |
| WO | 2012077116 | 6/2012 |
| WO | 2012077117 A1 | 6/2012 |
| WO | 2012096102 | 7/2012 |
| WO | 2012120507 A1 | 9/2012 |
| WO | 2013014673 | 1/2013 |
| WO | 2013024476 | 2/2013 |
| WO | 2014061023 | 4/2014 |
| WO | WO 2014/087745 A1 | 6/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

Notice of Allowance dated Apr. 18, 2017 for U.S. Appl. No. 13/713,449.
Office Action dated Apr. 19, 2017 for U.S. Appl. No. 14/988,551.
Notice of Allowability dated Apr. 21, 2017 for U.S. Appl. No. 14/549,265.
Office Action dated May 11, 2017 for U.S. Appl. No. 14/278,293.
Office Action dated May 10, 2017 for U.S. Appl. No. 14/988,551.
Office Action dated May 5, 2017 for U.S. Appl. No. 15/077,513.
Notice of Allowance dated May 15, 2017 for U.S. Appl. No. 14/271,270.
Office Action dated May 15, 2017 for U.S. Appl. No. 14/278,293.
Office Action dated May 18, 2017 for U.S. Appl. No. 14/278,338.
Notice of Allowance dated May 16, 2017 for U.S. Appl. No. 14/746,986.
Office Action dated May 23, 2017 for U.S. Appl. No. 13/655,120.
Notice of Allowance dated May 25, 2017 for U.S. Appl. No. 14/318,189.
Office Action dated May 23, 2017 for U.S. Appl. No. 14/500,975.
International Search Report for PCT/US14/37004, Sep. 25, 2014.
International Search Report for PCT/US14/38094, Nov. 6, 2014.
International Search Report for PCT/US2014/037526, Oct. 16, 2014.
International Search Report for PCT/US2014/071085, mailed on Mar. 27, 2015.
International Search Report for PCT/US2014/58143, mailed on Jan. 21, 2015.
International Search Report for PCT/US2015/012506, mailed on Dec. 11, 2015.
International Search Report for PCT/US2015/012751, mailed on Jun. 26, 2015.
International Search Report for PCT/US2015/027902, mailed on Jul. 23, 2015.
International Search Report for PCT/US2015/28962, mailed on Jul. 28, 2015.
International Search Report for PCT/US2015/29421, mailed on Aug. 7, 2015.
International Search Report for PCT/US2015/41396, mailed on Sep. 29, 2015.
International Search Report for PCT/US2015/47334, mailed on Dec. 28, 2015.
International Search Report for PCT/US2015/6548, mailed on Feb. 26, 2016.
International Search Report for PCT/US2015/66486, mailed on Dec. 17, 2015.

(56) References Cited

OTHER PUBLICATIONS

Olympus Operation Manual, GIF Type 160 Gastrointestinal Videoscope, 2003.
Olympus letter and chart, GI Endoscopes with Auxiliary Water Features, Mar. 3, 2003.
International Search Report for PCT/US2016/062713, Feb. 2, 2017.
Corrected Notice of Allowance dated Apr. 13, 2016 for U.S. Appl. No. 13/680,646.
Notice of Allowance dated Mar. 28, 2016 for U.S. Appl. No. 13/413,059.
Notice of Allowance dated Mar. 29, 2016 for U.S. Appl. No. 13/680,646.
Office Action date Feb. 26, 2016 for U.S. Appl. No. 14/274,323.
Office Action dated Feb. 4, 2016 for U.S. Appl. No. 14/271,234.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.
Office Action dated Jun. 30, 2016 for U.S. Appl. No. 13/655,120.
Office Action dated Jun. 28, 2016 for U.S. Appl. No. 14/278,293.
Office Action dated Jul. 1, 2016 for U.S. Appl. No. 14/229,699.
Office Action dated Jul. 15, 2016 for U.S. Appl. No. 14/273,923.
Notice of Allowance dated Jul. 15, 2016 for U.S. Appl. No. 14/274,323.
Office Action dated Jul. 22, 2016 for U.S. Appl. No. 14/549,265.
Sherman L.M., Plastics That Conduct Hear, Plastics Technology, Jun. 2001—article obtained online from http://www.ptonline.com/articles/plastics-that-conduct-heat.
Office Action dated Aug. 11, 2016 for U.S. Appl. No. 14/318,249.
Office Action dated Apr. 28, 2016 for U.S. Appl. No. 13/992,014.
Notice of Allowance dated Aug. 26, 2016 for U.S. Appl. No. 13/212,627.
Office Action dated Sep. 2, 2016 for U.S. Appl. No. 14/278,338.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Oct. 13, 2016 for U.S. Appl. No. 14/273,923.
Notice of Allowance dated Nov. 9, 2016 for U.S. Appl. No. 13/557,114.
Office Action dated Dec. 1, 2016 for U.S. Appl. No. 14/278,293.
Office Action dated Dec. 9, 2016 for U.S. Appl. No. 14/549,265.
Office Action dated Dec. 16, 2016 for U.S. Appl. No. 14/263,896.
Notice of Allowance dated Dec. 28, 2016 for U.S. Appl. No. 14/229,699.
Notice of Allowance dated Dec. 27, 2016 for U.S. Appl. No. 14/317,863.
Office Action dated Dec. 27, 2016 for U.S. Appl. No. 14/603,137.
Office Action dated Dec. 29, 2016 for U.S. Appl. No. 15/077,513.
Office Action dated Dec. 30, 2016 for U.S. Appl. No. 14/457,268.
Office Action dated Jan. 17, 2017 for U.S. Appl. No. 14/318,189.
Notice of Allowance dated Jan. 31, 2017 for U.S. Appl. No. 14/271,234.
Office Action dated Feb. 2, 2017 for U.S. Appl. No. 14/278,338.
Office Action dated Feb. 9, 2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Office Action dated Mar. 9, 2017 for U.S. Appl. No. 14/791,316.
Office Action dated Mar. 21, 2017 for U.S. Appl. No. 13/992,014.
Office Action mailed Mar. 20, 2017 for U.S. Appl. No. 14/278,293.
Notice of Allowance dated Mar. 21, 2017 for U.S. Appl. No. 14/549,265.
Office Action dated Mar. 22, 2017 for U.S. Appl. No. 14/705,355.
Office Action dated Mar. 24, 2017 for U.S. Appl. No. 14/838,509.
Japanese Office Action in corresponding Japanese Application No. 2021-203432, dated Feb. 1, 2023 (8 pages).

* cited by examiner

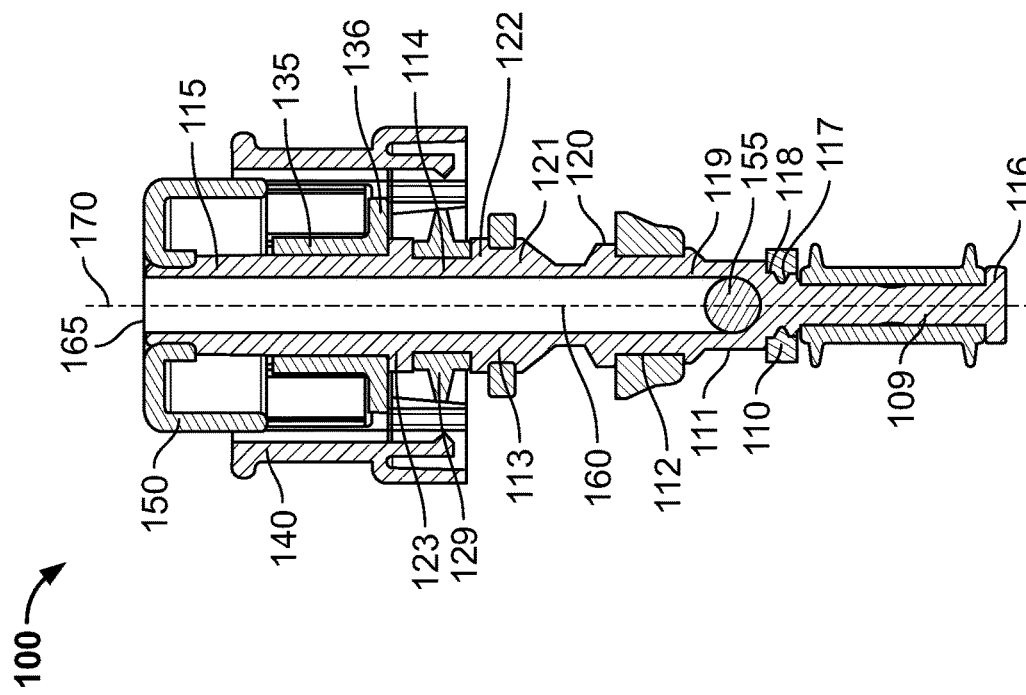
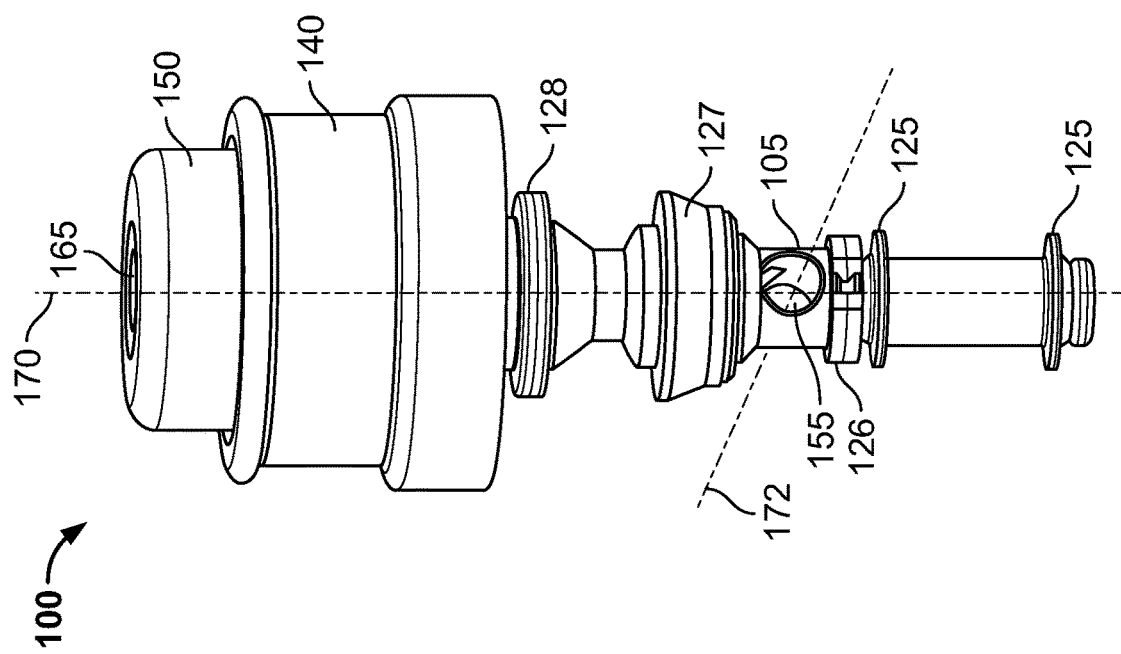

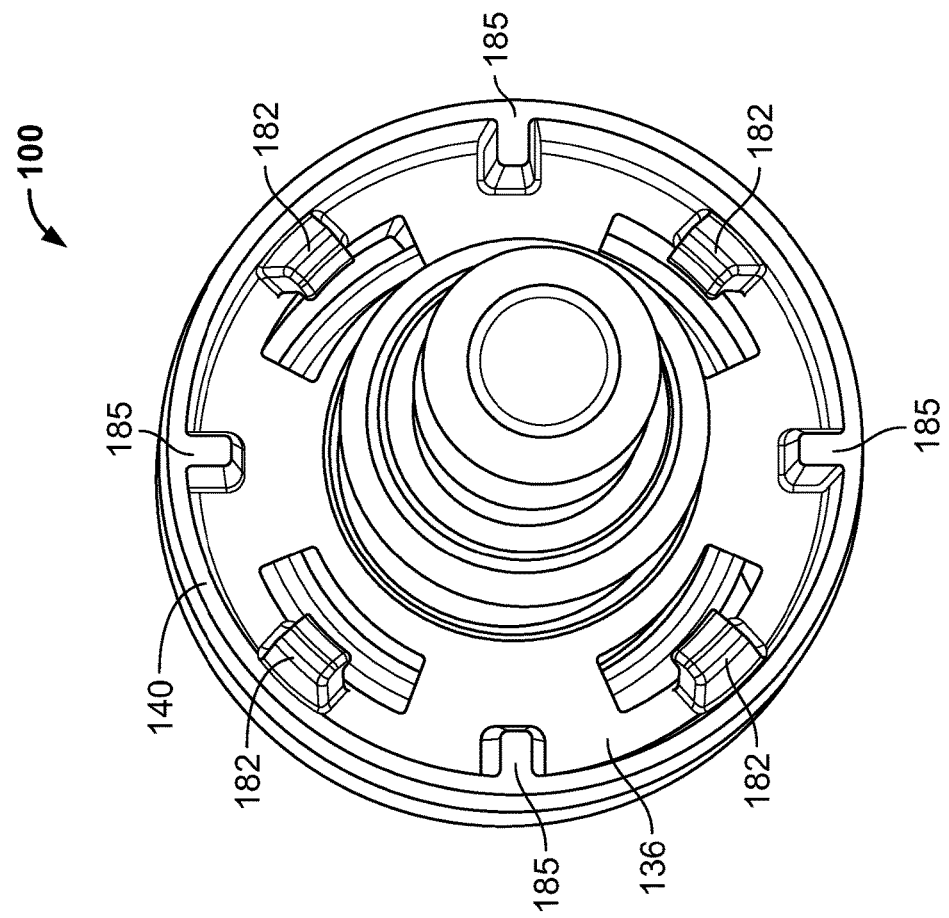
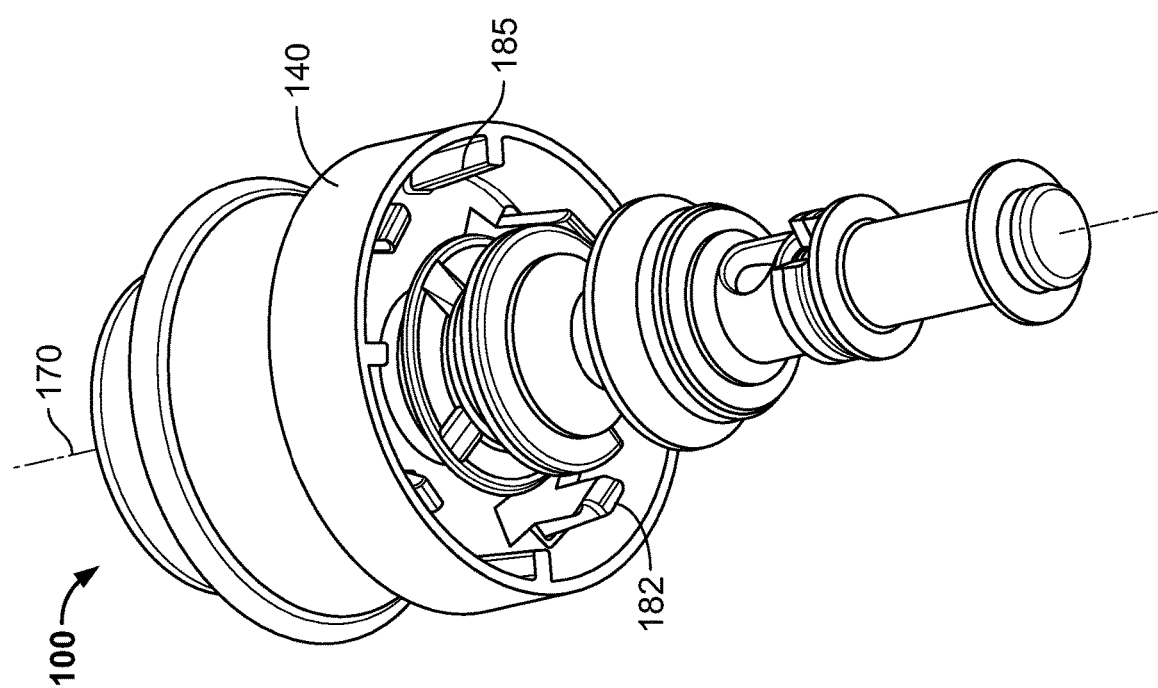
FIG. 1E
FIG. 1F

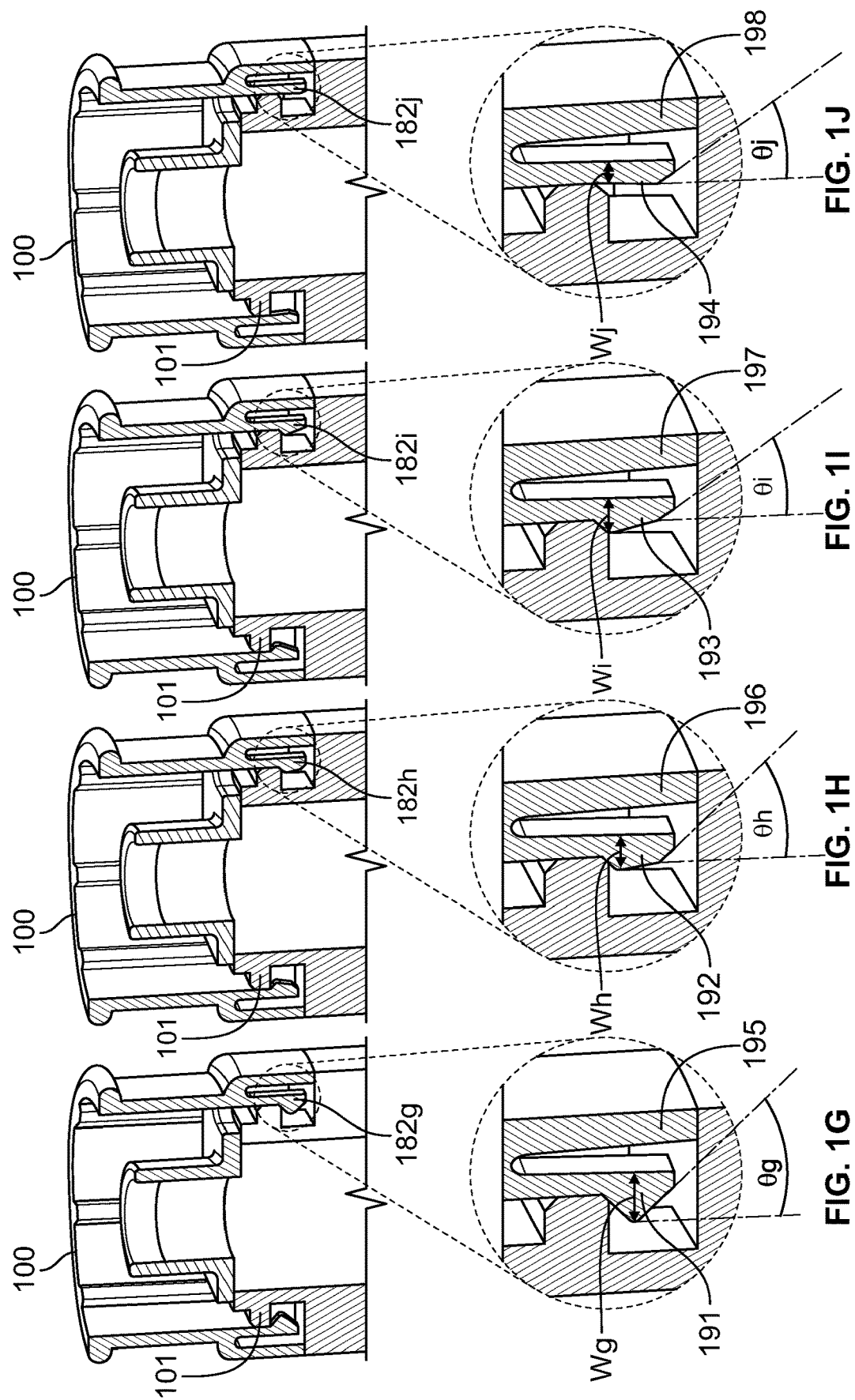

205

Air/Water Valve Insertion Force

| 140 STD Sample | Actual Force N | Expected Force N | Pass/Fail | Goal Force N | Pass/Fail | Type |
|---|---|---|---|---|---|---|
| 1 | 12.2 | ≤ 72N | Pass | ≤ 21.6N | Pass | 140 STD |
| 2 | 9.1 | ≤ 72N | Pass | ≤ 21.6N | Pass | 140 STD |
| 3 | 10.8 | ≤ 72N | Pass | ≤ 21.6N | Pass | 140 STD |
| 4 | 8.4 | ≤ 72N | Pass | ≤ 21.6N | Pass | 140 STD |
| 5 | 10.1 | ≤ 72N | Pass | ≤ 21.6N | Pass | 140 STD |
| Average | 10.1 | | | | | |
| Max | 12.2 | | | | | |
| Min | 8.4 | | | | | |

| 140 1/2 STD | Actual Force | Expected Force | | Goal Force | | |
|---|---|---|---|---|---|---|
| 6 | 8.9 | ≤ 72N | Pass | ≤ 21.6N | Pass | 140 1/2 STD |
| 7 | 8.1 | ≤ 72N | Pass | ≤ 21.6N | Pass | 140 1/2 STD |
| 8 | 9.6 | ≤ 72N | Pass | ≤ 21.6N | Pass | 140 1/2 STD |
| 9 | 8.7 | ≤ 72N | Pass | ≤ 21.6N | Pass | 140 1/2 STD |
| 10 | 9.6 | ≤ 72N | Pass | ≤ 21.6N | Pass | 140 1/2 STD |
| Average | 9.0 | | | | | |
| Max | 9.6 | | | | | |
| Min | 8.1 | | | | | |

| 140 WAVE | Actual Force | Expected Force | | Goal Force | | |
|---|---|---|---|---|---|---|
| 11 | 10.5 | ≤ 72N | Pass | ≤ 21.6N | Pass | 140 WAVE |
| 12 | 10.7 | ≤ 72N | Pass | ≤ 21.6N | Pass | 140 WAVE |
| 13 | 10.9 | ≤ 72N | Pass | ≤ 21.6N | Pass | 140 WAVE |
| 14 | 11.9 | ≤ 72N | Pass | ≤ 21.6N | Pass | 140 WAVE |
| 15 | 10.4 | ≤ 72N | Pass | ≤ 21.6N | Pass | 140 WAVE |
| Average | 10.9 | | | | | |
| Max | 11.9 | | | | | |
| Min | 10.4 | | | | | |

| 70 STD Sample | Actual Force N | Expected Force N | Pass/Fail | Goal Force N | Pass/Fail | Type |
|---|---|---|---|---|---|---|
| 16 | 9.6 | ≤ 72N | Pass | ≤ 21.6N | Pass | 70 STD |
| 17 | 9.6 | ≤ 72N | Pass | ≤ 21.6N | Pass | 70 STD |
| 18 | 7.4 | ≤ 72N | Pass | ≤ 21.6N | Pass | 70 STD |
| 19 | 9.4 | ≤ 72N | Pass | ≤ 21.6N | Pass | 70 STD |
| 20 | 9.7 | ≤ 72N | Pass | ≤ 21.6N | Pass | 70 STD |
| Average | 9.1 | | | | | |
| Max | 9.7 | | | | | |
| Min | 7.4 | | | | | |

| 70 1/2 STD | Actual Force | Expected Force | | Goal Force | | |
|---|---|---|---|---|---|---|
| 21 | 9.1 | ≤ 72N | Pass | ≤ 21.6N | Pass | 70 1/2 STD |
| 22 | 7.9 | ≤ 72N | Pass | ≤ 21.6N | Pass | 70 1/2 STD |
| 23 | 13.0 | ≤ 72N | Pass | ≤ 21.6N | Pass | 70 1/2 STD |
| 24 | 10.5 | ≤ 72N | Pass | ≤ 21.6N | Pass | 70 1/2 STD |
| 25 | 9.7 | ≤ 72N | Pass | ≤ 21.6N | Pass | 70 1/2 STD |
| Average | 10.0 | | | | | |
| Max | 13.0 | | | | | |
| Min | 7.9 | | | | | |

| 70 WAVE | Actual Force | Expected Force | | Goal Force | | |
|---|---|---|---|---|---|---|
| 26 | 13.0 | ≤ 72N | Pass | ≤ 21.6N | Pass | 70 WAVE |
| 27 | 8.2 | ≤ 72N | Pass | ≤ 21.6N | Pass | 70 WAVE |
| 28 | 10.5 | ≤ 72N | Pass | ≤ 21.6N | Pass | 70 WAVE |
| 29 | 11.7 | ≤ 72N | Pass | ≤ 21.6N | Pass | 70 WAVE |
| 30 | 12.3 | ≤ 72N | Pass | ≤ 21.6N | Pass | 70 WAVE |
| Average | 11.1 | | | | | |
| Max | 13.0 | | | | | |
| Min | 8.2 | | | | | |

| 35 STD Sample | Actual Force N | Expected Force N | Pass/Fail | Goal Force N | Pass/Fail | Type |
|---|---|---|---|---|---|---|
| 31 | 9.9 | ≤ 72N | Pass | ≤ 21.6N | Pass | 35 STD |
| 32 | 9.3 | ≤ 72N | Pass | ≤ 21.6N | Pass | 35 STD |
| 33 | 9.1 | ≤ 72N | Pass | ≤ 21.6N | Pass | 35 STD |
| 34 | 8.2 | ≤ 72N | Pass | ≤ 21.6N | Pass | 35 STD |
| 35 | 7.4 | ≤ 72N | Pass | ≤ 21.6N | Pass | 35 STD |
| Average | 8.8 | | | | | |
| Max | 9.9 | | | | | |
| Min | 7.4 | | | | | |

| 35 1/2 STD | Actual Force | Expected Force | | Goal Force | | |
|---|---|---|---|---|---|---|
| 36 | 6.4 | ≤ 72N | Pass | ≤ 21.6N | Pass | 35 1/2 STD |
| 37 | 9.5 | ≤ 72N | Pass | ≤ 21.6N | Pass | 35 1/2 STD |
| 38 | 6.8 | ≤ 72N | Pass | ≤ 21.6N | Pass | 35 1/2 STD |
| 39 | 8.8 | ≤ 72N | Pass | ≤ 21.6N | Pass | 35 1/2 STD |
| 40 | 7.1 | ≤ 72N | Pass | ≤ 21.6N | Pass | 35 1/2 STD |
| Average | 7.7 | | | | | |
| Max | 9.5 | | | | | |
| Min | 6.4 | | | | | |

| 35 WAVE | Actual Force | Expected Force | | Goal Force | | |
|---|---|---|---|---|---|---|
| 41 | 12.0 | ≤ 72N | Pass | ≤ 21.6N | Pass | 35 WAVE |
| 42 | 10.6 | ≤ 72N | Pass | ≤ 21.6N | Pass | 35 WAVE |
| 43 | 8.9 | ≤ 72N | Pass | ≤ 21.6N | Pass | 35 WAVE |
| 44 | 9.3 | ≤ 72N | Pass | ≤ 21.6N | Pass | 35 WAVE |
| 45 | 7.0 | ≤ 72N | Pass | ≤ 21.6N | Pass | 35 WAVE |
| Average | 9.6 | | | | | |
| Max | 12.0 | | | | | |
| Min | 7.0 | | | | | |

Air/Water Valve Removal Force

| 140 STD Sample | Actual Force N | Expected Force N | Pass/Fail | Goal Force N | Pass/Fail | Type |
|---|---|---|---|---|---|---|
| 1 | 5.81 | ≤ 72N | Pass | ≤ 8.1N | Pass | 140 STD |
| 2 | 14.23 | ≤ 72N | Pass | ≤ 8.1N | Fail | 140 STD |
| 3 | 8.91 | ≤ 72N | Pass | ≤ 8.1N | Fail | 140 STD |
| 4 | 8.54 | ≤ 72N | Pass | ≤ 8.1N | Fail | 140 STD |
| 5 | 7.10 | ≤ 72N | Pass | ≤ 8.1N | Pass | 140 STD |
| Average | 8.9 | | | | | |
| Max | 14.2 | | | | | |
| Min | 5.8 | | | | | |

| 140 1/2 STD | Actual Force | Expected Force | | Goal Force | | |
|---|---|---|---|---|---|---|
| 6 | 11.35 | ≤ 72N | Pass | ≤ 8.1N | Fail | 140 1/2 STD |
| 7 | 6.36 | ≤ 72N | Pass | ≤ 8.1N | Pass | 140 1/2 STD |
| 8 | 9.04 | ≤ 72N | Pass | ≤ 8.1N | Fail | 140 1/2 STD |
| 9 | 7.12 | ≤ 72N | Pass | ≤ 8.1N | Pass | 140 1/2 STD |
| 10 | 9.82 | ≤ 72N | Pass | ≤ 8.1N | Fail | 140 1/2 STD |
| Average | 8.7 | | | | | |
| Max | 11.4 | | | | | |
| Min | 6.4 | | | | | |

| 140 WAVE | Actual Force | Expected Force | | Goal Force | | |
|---|---|---|---|---|---|---|
| 11 | 6.10 | ≤ 72N | Pass | ≤ 8.1N | Pass | 140 WAVE |
| 12 | 11.58 | ≤ 72N | Pass | ≤ 8.1N | Fail | 140 WAVE |
| 13 | 12.19 | ≤ 72N | Pass | ≤ 8.1N | Fail | 140 WAVE |
| 14 | 6.40 | ≤ 72N | Pass | ≤ 8.1N | Pass | 140 WAVE |
| 15 | 10.98 | ≤ 72N | Pass | ≤ 8.1N | Fail | 140 WAVE |
| Average | 9.5 | | | | | |
| Max | 12.2 | | | | | |
| Min | 6.1 | | | | | |

| 70 STD Sample | Actual Force N | Expected Force N | Pass/Fail | Goal Force N | Pass/Fail | Type |
|---|---|---|---|---|---|---|
| 16 | 6.79 | ≤ 72N | Pass | ≤ 8.1N | Pass | 70 STD |
| 17 | 6.30 | ≤ 72N | Pass | ≤ 8.1N | Pass | 70 STD |
| 18 | 5.57 | ≤ 72N | Pass | ≤ 8.1N | Pass | 70 STD |
| 19 | 6.34 | ≤ 72N | Pass | ≤ 8.1N | Pass | 70 STD |
| 20 | 5.49 | ≤ 72N | Pass | ≤ 8.1N | Pass | 70 STD |
| Average | 6.1 | | | | | |
| Max | 6.8 | | | | | |
| Min | 5.5 | | | | | |

| 70 1/2 STD | Actual Force | Expected Force | | Goal Force | | |
|---|---|---|---|---|---|---|
| 21 | 6.04 | ≤ 72N | Pass | ≤ 8.1N | Pass | 70 1/2 STD |
| 22 | 9.16 | ≤ 72N | Pass | ≤ 8.1N | Fail | 70 1/2 STD |
| 23 | 6.06 | ≤ 72N | Pass | ≤ 8.1N | Pass | 70 1/2 STD |
| 24 | 5.28 | ≤ 72N | Pass | ≤ 8.1N | Pass | 70 1/2 STD |
| 25 | 5.05 | ≤ 72N | Pass | ≤ 8.1N | Pass | 70 1/2 STD |
| Average | 6.3 | | | | | |
| Max | 9.2 | | | | | |
| Min | 5.1 | | | | | |

| 70 WAVE | Actual Force | Expected Force | | Goal Force | | |
|---|---|---|---|---|---|---|
| 26 | 5.09 | ≤ 72N | Pass | ≤ 8.1N | Pass | 70 WAVE |
| 27 | 8.07 | ≤ 72N | Pass | ≤ 8.1N | Pass | 70 WAVE |
| 28 | 6.42 | ≤ 72N | Pass | ≤ 8.1N | Pass | 70 WAVE |
| 29 | 4.06 | ≤ 72N | Pass | ≤ 8.1N | Pass | 70 WAVE |
| 30 | 4.01 | ≤ 72N | Pass | ≤ 8.1N | Pass | 70 WAVE |
| Average | 5.5 | | | | | |
| Max | 8.1 | | | | | |
| Min | 4.0 | | | | | |

| 35 STD Sample | Actual Force N | Expected Force N | Pass/Fail | Goal Force N | Pass/Fail | Type |
|---|---|---|---|---|---|---|
| 31 | 6.46 | ≤ 72N | Pass | ≤ 8.1N | Pass | 35 STD |
| 32 | 6.57 | ≤ 72N | Pass | ≤ 8.1N | Pass | 35 STD |
| 33 | 4.46 | ≤ 72N | Pass | ≤ 8.1N | Pass | 35 STD |
| 34 | 5.97 | ≤ 72N | Pass | ≤ 8.1N | Pass | 35 STD |
| 35 | 4.50 | ≤ 72N | Pass | ≤ 8.1N | Pass | 35 STD |
| Average | 5.6 | | | | | |
| Max | 6.6 | | | | | |
| Min | 4.5 | | | | | |

| 35 1/2 STD | Actual Force | Expected Force | | Goal Force | | |
|---|---|---|---|---|---|---|
| 36 | 5.58 | ≤ 72N | Pass | ≤ 8.1N | Pass | 35 1/2 STD |
| 37 | 5.44 | ≤ 72N | Pass | ≤ 8.1N | Pass | 35 1/2 STD |
| 38 | 5.38 | ≤ 72N | Pass | ≤ 8.1N | Pass | 35 1/2 STD |
| 39 | 6.28 | ≤ 72N | Pass | ≤ 8.1N | Pass | 35 1/2 STD |
| 40 | 5.48 | ≤ 72N | Pass | ≤ 8.1N | Pass | 35 1/2 STD |
| Average | 5.6 | | | | | |
| Max | 6.3 | | | | | |
| Min | 5.4 | | | | | |

| 35 WAVE | Actual Force | Expected Force | | Goal Force | | |
|---|---|---|---|---|---|---|
| 41 | 5.42 | ≤ 72N | Pass | ≤ 8.1N | Pass | 35 WAVE |
| 42 | 5.03 | ≤ 72N | Pass | ≤ 8.1N | Pass | 35 WAVE |
| 43 | 6.28 | ≤ 72N | Pass | ≤ 8.1N | Pass | 35 WAVE |
| 44 | 5.66 | ≤ 72N | Pass | ≤ 8.1N | Pass | 35 WAVE |
| 45 | 6.05 | ≤ 72N | Pass | ≤ 8.1N | Pass | 35 WAVE |
| Average | 5.7 | | | | | |
| Max | 6.3 | | | | | |
| Min | 5.0 | | | | | |

| | | | Air/Water Valve Depression Force | | | | | Depression Distance | | |
|---|---|---|---|---|---|---|---|---|---|---|
| 140 STD Sample | Actual Force N | Expected Force N | Pass/Fail | Goal Force N | Pass/Fail | | Actual Distance mm | Expected Distance mm | Pass/Fail | Type |
| 1 | 20.95 | 6.4N - 42N | Pass | 9.6N - 14.4N | Fail | | 4.58 | 2 - 5 | Pass | 140 STD |
| 2 | 16.31 | 6.4N - 42N | Pass | 9.6N - 14.6N | Fail | | -13.7 | 2 - 5 | Pass | 140 STD |
| 3 | 17.03 | 6.4N - 42N | Pass | 9.6N - 14.4N | Fail | | 4.58 | 2 - 5 | Pass | 140 STD |
| 4 | 15.28 | 6.4N - 42N | Pass | 9.6N - 14.6N | Fail | | 4.58 | 2 - 5 | Pass | 140 STD |
| 5 | 17.18 | 6.4N - 42N | Pass | 9.6N - 14.4N | Fail | | 4.58 | 2 - 5 | Pass | 140 STD |
| Average | 17.35 | | | | | Average | 0.92 | | | |
| Max | 20.95 | | | | | Max | 4.58 | | | |
| Min | 15.28 | | | | | Min | -13.70 | | | |

| 140 1/2 STD Sample | Actual Force N | Expected Force N | Pass/Fail | Goal Force N | Pass/Fail | | Actual Distance mm | Expected Distance mm | Pass/Fail | Type |
|---|---|---|---|---|---|---|---|---|---|---|
| 6 | 11.61 | 6.4N - 42N | Pass | 9.6N - 14.6N | Pass | | 4.58 | 2 - 5 | Pass | 140 1/2 STD |
| 7 | 10.41 | 6.4N - 42N | Pass | 9.6N - 14.4N | Pass | | 4.58 | 2 - 5 | Pass | 140 1/2 STD |
| 8 | 9.28 | 6.4N - 42N | Pass | 9.6N - 14.6N | Fail | | 4.58 | 2 - 5 | Pass | 140 1/2 STD |
| 9 | 10.10 | 6.4N - 42N | Pass | 9.6N - 14.4N | Pass | | 4.58 | 2 - 5 | Pass | 140 1/2 STD |
| 10 | 9.15 | 6.4N - 42N | Pass | 9.6N - 14.6N | Fail | | 4.58 | 2 - 5 | Pass | 140 1/2 STD |
| Average | 10.11 | | | | | Average | 4.58 | | | |
| Max | 11.61 | | | | | Max | 4.58 | | | |
| Min | 9.15 | | | | | Min | 4.58 | | | |

FIG. 3D

| 140 WAVE | Actual Force | Expected Force | | Goal Force | | Actual Distance | Expected Distance | | Type |
|---|---|---|---|---|---|---|---|---|---|
| Sample | N | N | Pass/Fail | N | Pass/Fail | mm | mm | Pass/Fail | |
| 11 | 13.71 | 6.4N - 42N | Pass | 9.6N - 14.4N | Pass | 5.09 | 2 - 5 | Pass | 140 WAVE |
| 12 | 11.02 | 6.4N - 42N | Pass | 9.6N - 14.6N | Pass | 5.09 | 2 - 5 | Pass | 140 WAVE |
| 13 | 11.95 | 6.4N - 42N | Pass | 9.6N - 14.4N | Pass | 5.09 | 2 - 5 | Pass | 140 WAVE |
| 14 | 12.04 | 6.4N - 42N | Pass | 9.6N - 14.6N | Pass | 5.09 | 2 - 5 | Pass | 140 WAVE |
| 15 | 13.56 | 6.4N - 42N | Pass | 9.6N - 14.4N | Pass | 5.09 | 2 - 5 | Pass | 140 WAVE |
| Average | 12.46 | | | | | 5.09 | | | |
| Max | 13.71 | | | | | 5.09 | | | |
| Min | 11.02 | | | | | 5.09 | | | |

| 70 STD | Actual Force | Expected Force | | Goal Force | | Actual Distance | Expected Distance | | Type |
|---|---|---|---|---|---|---|---|---|---|
| Sample | N | N | Pass/Fail | N | Pass/Fail | mm | mm | Pass/Fail | |
| 16 | 13.55 | 6.4N - 42N | Pass | 9.6N - 14.6N | Pass | 4.58 | 2 - 5 | Pass | 70 STD |
| 17 | 12.87 | 6.4N - 42N | Pass | 9.6N - 14.4N | Pass | 4.58 | 2 - 5 | Pass | 70 STD |
| 18 | 18.94 | 6.4N - 42N | Pass | 9.6N - 14.6N | Fail | 4.58 | 2 - 5 | Pass | 70 STD |
| 19 | 17.89 | 6.4N - 42N | Pass | 9.6N - 14.4N | Fail | 4.58 | 2 - 5 | Pass | 70 STD |
| 20 | 13.21 | 6.4N - 42N | Pass | 9.6N - 14.6N | Pass | 4.58 | 2 - 5 | Pass | 70 STD |
| Average | 15.29 | | | | | 4.58 | | | |
| Max | 18.94 | | | | | 4.58 | | | |
| Min | 12.87 | | | | | 4.58 | | | |

| 70 1/2 STD | Actual Force | Expected Force | | Goal Force | | Actual Distance | Expected Distance | | Type |
|---|---|---|---|---|---|---|---|---|---|
| Sample | N | N | Pass/Fail | N | Pass/Fail | mm | mm | Pass/Fail | |
| 21 | 18.52 | 6.4N - 42N | Pass | 9.6N - 14.4N | Fail | 5.09 | 2 - 5 | Pass | 70 1/2 STD |
| 22 | 15.74 | 6.4N - 42N | Pass | 9.6N - 14.6N | Fail | 5.09 | 2 - 5 | Pass | 70 1/2 STD |
| 23 | 9.73 | 6.4N - 42N | Pass | 9.6N - 14.4N | Pass | 5.09 | 2 - 5 | Pass | 70 1/2 STD |
| 24 | 13.67 | 6.4N - 42N | Pass | 9.6N - 14.6N | Pass | 5.09 | 2 - 5 | Pass | 70 1/2 STD |
| 25 | 13.44 | 6.4N - 42N | Pass | 9.6N - 14.4N | Pass | 5.09 | 2 - 5 | Pass | 70 1/2 STD |
| Average | 14.22 | | | | | 5.09 | | | |
| Max | 18.52 | | | | | 5.09 | | | |
| Min | 9.73 | | | | | 5.09 | | | |

FIG. 3E

| 70 WAVE | Actual Force | Expected Force | | Goal Force | | Actual Distance | Expected Distance | | Type |
|---|---|---|---|---|---|---|---|---|---|
| Sample | N | N | Pass/Fail | N | Pass/Fail | mm | mm | Pass/Fail | Type |
| 26 | 10.44 | 6.4N - 42N | Pass | 9.6N - 14.6N | Pass | 4.58 | 2 - 5 | Pass | 70 WAVE |
| 27 | 9.78 | 6.4N - 42N | Pass | 9.6N - 14.4N | Pass | 4.58 | 2 - 5 | Pass | 70 WAVE |
| 28 | 9.75 | 6.4N - 42N | Pass | 9.6N - 14.6N | Pass | 4.58 | 2 - 5 | Pass | 70 WAVE |
| 29 | 10.24 | 6.4N - 42N | Pass | 9.6N - 14.4N | Pass | 4.58 | 2 - 5 | Pass | 70 WAVE |
| 30 | 9.40 | 6.4N - 42N | Pass | 9.6N - 14.6N | Fail | 4.58 | 2 - 5 | Pass | 70 WAVE |
| Average | 9.92 | | | | | Average | 4.58 | | |
| Max | 10.44 | | | | | Max | 4.58 | | |
| Min | 9.40 | | | | | Min | 4.58 | | |

| 35 STD Sample | Actual Force N | Expected Force N | Pass/Fail | Goal Force N | Pass/Fail | Actual Distance mm | Expected Distance mm | Pass/Fail | Type |
|---|---|---|---|---|---|---|---|---|---|
| 31 | 11.94 | 6.4N - 42N | Pass | 9.6N - 14.6N | Pass | 5.09 | 2 - 5 | Pass | 35 STD |
| 32 | 12.65 | 6.4N - 42N | Pass | 9.6N - 14.6N | Pass | 5.09 | 2 - 5 | Pass | 35 STD |
| 33 | 12.50 | 6.4N - 42N | Pass | 9.6N - 14.6N | Pass | 5.09 | 2 - 5 | Pass | 35 STD |
| 34 | 12.26 | 6.4N - 42N | Pass | 9.6N - 14.6N | Pass | 5.09 | 2 - 5 | Pass | 35 STD |
| 35 | 12.44 | 6.4N - 42N | Pass | 9.6N - 14.6N | Pass | 5.09 | 2 - 5 | Pass | 35 STD |
| Average | 12.36 | | | | | 5.09 | | | |
| Max | 12.65 | | | | | 5.09 | | | |
| Min | 11.94 | | | | | 5.09 | | | |

| 35 1/2 STD Sample | Actual Force N | Expected Force N | Pass/Fail | Goal Force N | Pass/Fail | Actual Distance mm | Expected Distance mm | Pass/Fail | Type |
|---|---|---|---|---|---|---|---|---|---|
| 36 | 10.84 | 6.4N - 42N | Pass | 9.6N - 14.6N | Pass | 5.09 | 2 - 5 | Pass | 35 1/2 STD |
| 37 | 11.02 | 6.4N - 42N | Pass | 9.6N - 14.6N | Pass | 5.09 | 2 - 5 | Pass | 35 1/2 STD |
| 38 | 11.19 | 6.4N - 42N | Pass | 9.6N - 14.6N | Pass | 5.09 | 2 - 5 | Pass | 35 1/2 STD |
| 39 | 14.78 | 6.4N - 42N | Pass | 9.6N - 14.6N | Fail | 4.58 | 2 - 5 | Pass | 35 1/2 STD |
| 40 | 12.55 | 6.4N - 42N | Pass | 9.6N - 14.6N | Pass | 4.58 | 2 - 5 | Pass | 35 1/2 STD |
| Average | 12.08 | | | | | 4.89 | | | |
| Max | 14.78 | | | | | 5.09 | | | |
| Min | 10.84 | | | | | 4.58 | | | |

FIG. 3F

| 35 WAVE | Actual Force | Expected Force | | Goal Force | | Actual Distance | Expected Distance | | |
|---|---|---|---|---|---|---|---|---|---|
| Sample | N | N | Pass/Fail | N | Pass/Fail | mm | mm | Pass/Fail | Type |
| 41 | 10.68 | 6.4N - 42N | Pass | 9.6N - 14.6N | Pass | 4.58 | 2 - 5 | Pass | 35 WAVE |
| 42 | 10.65 | 6.4N - 42N | Pass | 9.6N - 14.6N | Pass | 4.58 | 2 - 5 | Pass | 35 WAVE |
| 43 | 11.73 | 6.4N - 42N | Pass | 9.6N - 14.6N | Pass | 4.58 | 2 - 5 | Pass | 35 WAVE |
| 44 | 15.26 | 6.4N - 42N | Pass | 9.6N - 14.6N | Fail | 4.58 | 2 - 5 | Pass | 35 WAVE |
| 45 | 13.38 | 6.4N - 42N | Pass | 9.6N - 14.6N | Pass | 4.58 | 2 - 5 | Pass | 35 WAVE |
| Average | 12.34 | | | | | Average | 4.58 | | |
| Max | 15.26 | | | | | Max | 4.58 | | |
| Min | 10.65 | | | | | Min | 4.58 | | |

FIG. 3F(Cont.)

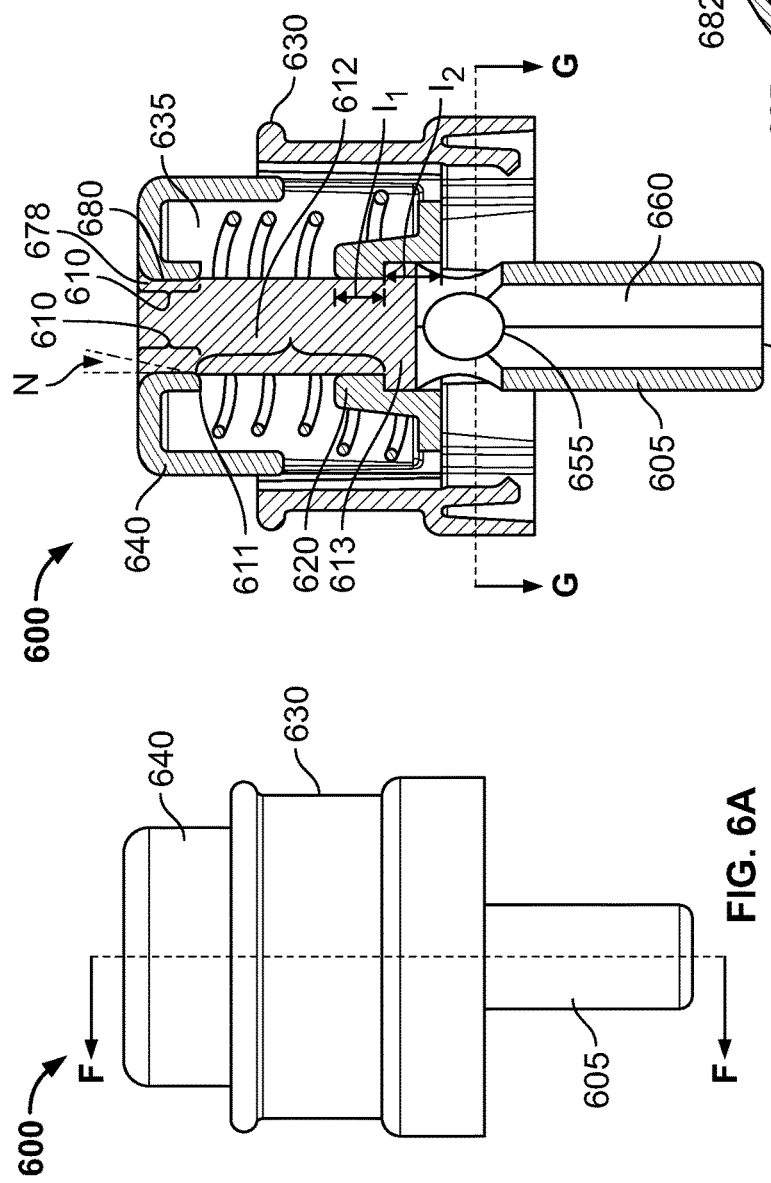
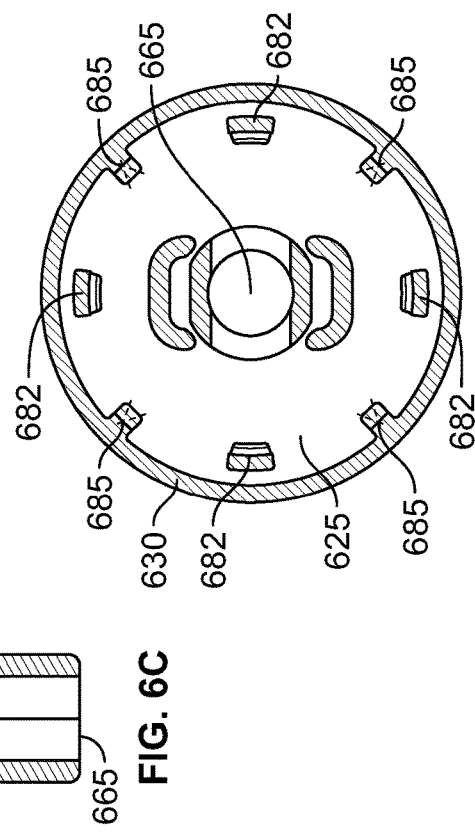
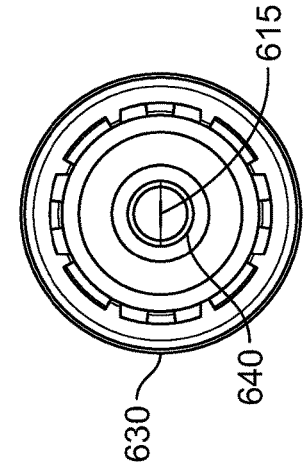

DISPOSABLE AIR/WATER AND SUCTION VALVES FOR AN ENDOSCOPE

CROSS-REFERENCE

This application is a continuation of U.S. Nonprovisional patent application Ser. No. 16/680,025, filed on Nov. 11, 2019, which is a continuation of U.S. Nonprovisional patent application Ser. No. 15/355,390, filed on Nov. 18, 2016, now U.S. Pat. No. 10,898,062, issued Jan. 26, 2021, which claims the benefit of U.S. Provisional Patent Application No. 62/259,573, filed on Nov. 24, 2015, and U.S. Provisional Patent Application No. 62/375,359, filed on Aug. 15, 2016. Each of the above-mentioned applications is herein incorporated by reference in its entirety.

FIELD

The present specification relates generally to endoscopy systems and more particularly, to disposable air/water and suction valves for use with an endoscope.

BACKGROUND

Endoscopes have attained great acceptance within the medical community since they provide a means for performing procedures with minimal patient trauma while enabling the physician to view the internal anatomy of the patient. Over the years, numerous endoscopes have been developed and categorized according to specific applications, such as cystoscopy, colonoscopy, laparoscopy, and upper GI endoscopy and others. Endoscopes may be inserted into the body's natural orifices or through an incision in the skin.

An endoscope usually includes an elongated tubular shaft, rigid or flexible, having a video camera or a fiber optic lens assembly at its distal end. The shaft is connected to a handle which sometimes includes an ocular element for direct viewing. Viewing may also be possible via an external screen. Various surgical tools may be inserted through a working channel in the endoscope for performing different surgical procedures. Often, the endoscope also has fluid injectors ("jet") for cleaning a body cavity, such as the colon, into which they are inserted. A control section of the endoscope may include a suction cylinder and an air/water cylinder. Valves may be inserted into these cylinders to control various functions of the endoscope.

For example, an air/water valve for an endoscope may be inserted into the air/water cylinder or channel of the endoscope to provide air and water to the endoscope. When the air/water valve is in a first, normal position, air escapes from a vent in the valve. When insufflation is desired, an operator places a finger over the vent, which redirects the air towards the distal end of the endoscope, thus insufflating the organ that is being examined. When the operator engages the air/water valve (e.g. by depressing the valve), air is redirected to a water bottle and creates pressure in the bottle that causes water to flow towards the distal end of the endoscope.

In addition, a suction valve for the endoscope may be inserted into the suction cylinder or channel of the endoscope to provide suction to the endoscope. When the suction valve is in a first, normal position, air flow from the distal tip of the endoscope is blocked by the valve. When suction is desired, an operator engages the suction valve (e.g. by depressing the valve) to open the suction channel to create negative pressure that draws air or fluid into the opening of the instrument channel of the endoscope. When the operator releases the suction valve, the valve returns to its normal position blocking air flow and stops the suctioning.

After each use, an endoscope must be cleaned, disinfected, and sterilized to prevent the spread of disease, germs, bacteria and illness. Many components of an endoscope may be reusable, such as the air/water valve and suction valve and thus, must also be cleaned, disinfected, and/or sterilized between uses. Unfortunately, there is usually a great expense associated with maintaining sterility of the equipment. In addition, since reusable air/water and suction valves may be assembled from a combination of several metal, plastic, and/or rubber components there are significant costs associated with the manufacturing of reusable air/water valves.

Accordingly, there is a need for single-use or disposable air/water and suction valves that can be easily manufactured and assembled using a variety of materials for various components of the valves. Additionally, disposable air/water and suction valves do not require expensive materials to fabricate the valves, thereby eliminating the high cost of manufacturing suction valves from expensive materials.

SUMMARY

The following embodiments and aspects thereof are described and illustrated in conjunction with systems, tools and methods, which are meant to be exemplary and illustrative, not limiting in scope. The present application discloses numerous embodiments.

The present specification discloses a disposable air and water valve for an endoscope, comprising: a shaft having a passage from a first opening to a vent, wherein the shaft has at least one groove, at least one ridge, and at least one protrusion formed at the vent; at least one seal set within the at least one groove; an outer cap; an inner ring having a diaphragm that extends from an outer circumference of the inner ring to an internal circumference of the outer cap, wherein at least one hinge extends vertically downwards from said diaphragm and wherein at least one rib is positioned along the internal circumference of the outer cap; a button cap having an internal ring that securely attaches to the shaft by fitting into a notch near the vent of the shaft; and a resilient member securely disposed between the button cap and the diaphragm, wherein the outer cap, inner ring, and internal ring of the button cap define a central bore to accommodate said shaft.

Optionally, the disposable air/water valve further comprises at least one bushing set within the at least one groove or a second groove, wherein said at least one bushing is configured to center said valve within a channel of an endoscope.

The shaft, seals, outer cap, inner ring, and button cap may comprise at least one of polyurethane, polyurea, polyether (amide), PEBA, thermoplastic elastomeric olefin, copolyester, styrenic thermoplastic elastomer, carbon fiber, glass fiber, ceramics, methacrylates, poly (N-isopropylacrylamide), PEO-PPO-PEO, rubber, plastic, polycarbonate, ABS, MABS, and silicone.

The resilient member may comprise at least one of a corrosion resistant metal, polyurethane, polyurea, polyether (amide), PEBA, thermoplastic elastomeric olefin, copolyester, and styrenic thermoplastic elastomer, carbon fiber, glass fiber, ceramics, methacrylates, poly (N-isopropylacrylamide), PEO-PPO-PEO, rubber, and plastic.

Optionally, the shaft comprises machined steel and said button cap comprises plastic and said shaft is mechanically bonded to said button cap.

Optionally, the at least one hinge comprises a tine and barb wherein the barb has a width of less than 200 microns.

Optionally, the at least one hinge is configured to connect to a corresponding mount on an endoscope and prevent vertical displacement of said at least one seal. Optionally, said at least one hinge is configured to generate an audible and tactile snap when said at least one hinge is connected to said corresponding mount, thereby indicating that the valve has been seated correctly.

Optionally, the at least one rib is configured to act as an edge stop to ensure said valve is centered on the mount and prevent a side loading from breaking said at least one seal.

Optionally, the outer cap and said inner ring with said at least one hinge and said at least one rib are molded as a single component.

The present specification also discloses a disposable suction valve for an endoscope, comprising: a shaft having a passage from a first opening to a vent, wherein the shaft has a plurality of grooves, a plurality of ridges and a protrusion formed at the vent; an outer cap; an inner ring having a diaphragm that extends from an outer circumference of the inner ring to an internal circumference of the outer cap, wherein a plurality of vertical hinges extend downward from said diaphragm and wherein a plurality of vertical ribs are formed along the internal circumference of the outer cap; a button cap having an internal ring configured to securely attach to the shaft; and a resilient member securely disposed between the button cap and the diaphragm, wherein the outer cap, inner ring, and internal ring of the button cap define a central bore to accommodate the shaft.

Optionally, the internal ring securely attaches to the shaft by fitting into a tapered notch near the vent of the shaft.

Optionally, each of the plurality of hinges comprises a tine and a barb. Optionally, the barb is defined by a width of less than 200 microns.

Optionally, said plurality of hinges is configured to connect to a corresponding mount on an endoscope. Optionally, each of said plurality of hinges is configured to generate an audible and tactile snap when each of said plurality of hinges connects to said corresponding mount.

Optionally, each of said plurality of vertical ribs is configured to act as an edge stop to ensure said valve is centered on the mount.

Optionally, the outer cap and said inner ring with said plurality of hinges and said plurality of ribs are molded as a single component.

The present specification also discloses a method of operating a disposable air/water valve for an endoscope comprising an air channel and a water channel each connected to a water bottle, said method comprising: placing a disposable air and water valve in a port of an endoscope wherein said disposable air and water valve comprises: a shaft having a passage from a first opening to a vent, wherein the shaft has a plurality of grooves, a plurality of ridges, and a protrusion formed at the vent; a plurality of seals set within at least a portion of the plurality of grooves; an outer cap; an inner ring having a diaphragm that extends from an outer circumference of the inner ring to an internal circumference of the outer cap, wherein a plurality of hinges extend vertically downwards from said diaphragm and wherein a plurality of ribs are formed along the internal circumference of the outer cap; a button cap having an internal ring configured to securely attach to the shaft; and a member securely disposed between the button cap and the diaphragm, wherein the outer cap, inner ring, and internal ring of the button cap define a central bore to accommodate the shaft; allowing air to enter at said first opening and escape from said vent when valve is un-actuated; covering said vent to force air through said air channel in a distal direction to insufflate a body cavity; actuating said valve by depressing said button cap to compress said resilient member and move said first opening into said water channel, forcing air into said water bottle and resulting in water being forced through said water channel in a distal direction; and releasing said button cap to allow said resilient member to decompress, move said first opening out of alignment with said water channel, un-actuate said valve and stop said flow of water.

The present specification also discloses a method of operating a disposable suction valve for an endoscope connected to a suction pump, said method comprising: placing a disposable suction valve in a suction cylinder of an endoscope wherein said disposable suction valve comprises: a shaft having a passage from a first opening to a vent, wherein the shaft has a plurality of grooves, a plurality of ridges and a protrusion formed at the vent; an inner ring having a diaphragm that extends from an outer circumference of the inner ring, wherein at least one hinge extends downward from said diaphragm; a button cap with an internal ring configured to securely attach to the shaft; and a resilient member securely disposed between the button cap and the diaphragm; preventing the suction pump from preventing negative pressure in the suction channel by not actuating said suction valve; actuating said suction valve by depressing said button cap to compress said resilient member and move said first opening into alignment with said suction channel, allowing said suction pump to create negative pressure in said suction channel to suction air and/or fluid from a distal end of said endoscope; and releasing said button cap to allow said resilient member to decompress to thereby move said first opening out of alignment with said suction channel, un-actuate said valve and stop said suction.

The aforementioned and other embodiments of the present shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein:

FIG. 1A is a perspective view of a single use, disposable air/water valve in accordance with an embodiment of the present specification;

FIG. 1B is a cross-section view of the air/water valve of FIG. 1A;

FIG. 1E is a bottom perspective view of the air/water valve of FIG. 1A;

FIG. 1F is a bottom view of the air/water valve of FIG. 1A;

FIG. 1G illustrates a first hinge or hook configured to enable a first amount of insertion/removal force, in accordance with an embodiment;

FIG. 1H illustrates a second hinge or hook configured to enable a second amount of insertion/removal force, in accordance with an embodiment;

FIG. 1I illustrates a third hinge or hook configured to enable a third amount of insertion/removal force, in accordance with an embodiment;

FIG. 1J illustrates a fourth hinge or hook configured to enable a fourth amount of insertion/removal force, in accordance with an embodiment;

FIG. 2A is a table showing an air/water valve insertion force for a 140 micron hook;

FIG. 2B is a table showing an air/water valve insertion force for a 70 micron hook;

FIG. 2C is a table showing an air/water valve insertion force for a 35 micron hook;

FIG. 2D is a table showing an air/water valve removal force for a 140 micron hook;

FIG. 2E is a table showing an air/water valve removal force for a 70 micron hook;

FIG. 2F is a table showing an air/water valve removal force for a 35 micron hook;

FIG. 3D is a table showing an air/water valve depression force for a 140 micron hook;

FIG. 3E is a table showing an air/water valve depression force for a 70 micron hook;

FIG. 3F is a table showing an air/water valve depression force for a 35 micron hook;

FIG. 6A is a perspective view of a disposable suction valve in accordance with an embodiment of the present specification;

FIG. 6B is a top view of the disposable suction valve of FIG. 6A;

FIG. 6C is a vertical cross-section view along an axis F-F of the disposable suction valve of FIG. 6A;

FIG. 6D is a horizontal cross-section view along an axis G-G of the disposable suction valve of FIG. 6C;

DETAILED DESCRIPTION

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. In the description and claims of the application, each of the words "comprise" "include" and "have", and forms thereof, are not necessarily limited to members in a list with which the words may be associated.

It should be noted herein that any feature or component described in association with a specific embodiment may be used and implemented with any other embodiment unless clearly indicated otherwise.

As used herein, the indefinite articles "a" and "an" mean "at least one" or "one or more" unless the context clearly dictates otherwise.

It is noted that the term "endoscope" as mentioned to herein may refer particularly to colonoscopes and gastroscopes, according to some embodiments, but is not limited only to colonoscopes and gastroscopes. The term "endoscope" may refer to any instrument used to examine the interior of a hollow organ or cavity of the body.

Figure 1D:
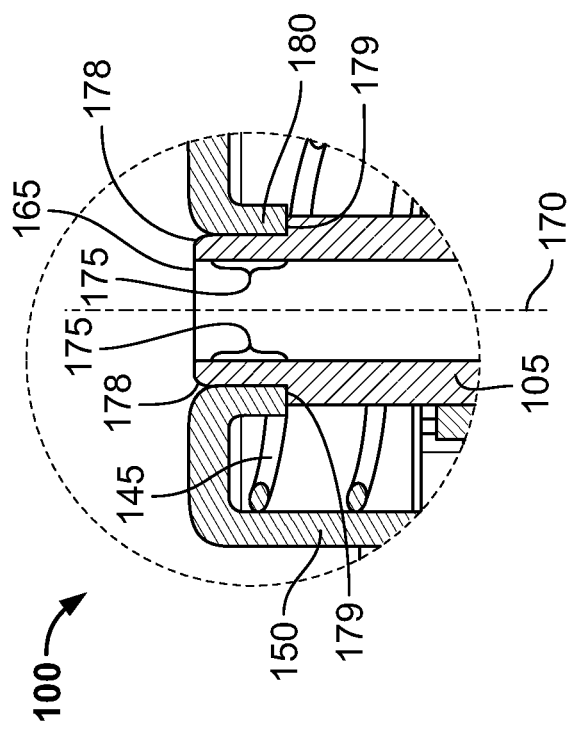
FIG. 1D is yet another cross-section view of the air/water valve of FIG. 1A.
Figure 1C:
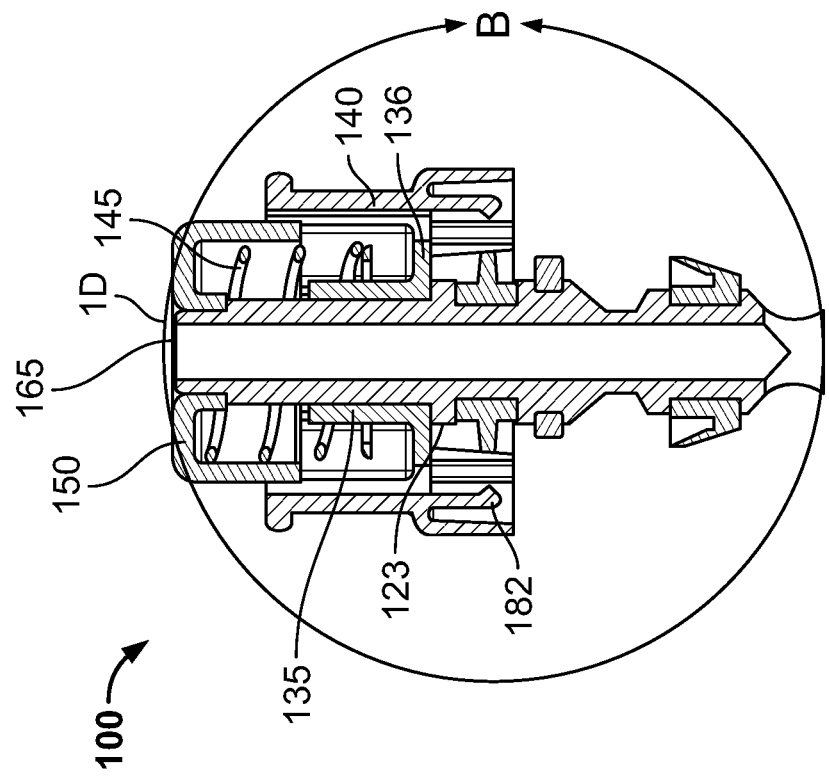
FIG. 1C is another cross-section view of the air/water valve of FIG. 1A.

FIG. 1A is a perspective view of a disposable air/water valve 100 in accordance with an embodiment of the present specification while FIGS. 1B, 1C and 1D are respectively first, second and third cross-section views of the air/water valve 100. Referring now to FIGS. 1A through 1D, the air/water valve 100 comprises a stem or shaft 105 having a plurality of grooves 109, 110, 111, 112, 113, 114, 115 and ridges 116, 117, 118, 119, 120, 121, 122, 123 that are molded or machined, in various embodiments, as part of the shaft 105. A plurality of seals 125, 127, and 129 may be set into the respective grooves 109, 112, 114 in accordance with some embodiments. A plurality of bushings 126, 128 may be set into respective grooves 110, 113 in accordance with some embodiments. The bushings 126, 128 assist in centering the air/water valve 100 in a channel within an endoscope. In various embodiments, the bushings 126, 128 are rigid or semi-rigid. In some embodiments, the air/water valve includes two bushings 126, 128 positioned in grooves 110, 113 respectively. In other embodiments, the air/water valve 100 includes only bushing 126 positioned in groove 110. In other embodiments, the device does not have bushings and, instead, rely on ribs to center the valve appropriately. In addition, air/water valve 100 may also comprise inner ring 135, outer cap 140, resilient member 145 (FIG. 1C, 1D) such as, but not limited to, spring, rubber, elastic, and a button cap 150.

In accordance with aspects of the present specification, the ridge 116 prevents unintentional removal of the seal 125 by providing an additional interference between the seal 125 and the shaft 105. In various embodiments, the shaft 105 has a preferred travel direction (from the ridge 116 toward the end 165) which enables an easier placement of the seal 125 than removal of the seal due to a direction of taper of the ridge 116.

The components of air/water valve 100 may comprise at least one disposable material, including, but not limited to polyurethane, polyurea, polyether(amide), PEBA, thermoplastic elastomeric olefin, copolyester, styrenic thermoplastic elastomer, carbon fiber, glass fiber, ceramics, methacrylates, poly (N-isopropylacrylamide), PEO-PPO-PEO (pluronics), rubber, plastic (e.g., polycarbonates), ABS, MABS, silicone, or combinations thereof. The resilient member 145 may be formed from a suitable material, such as corrosion resistant metal, polyurethane, polyurea, polyether(amide), PEBA, thermoplastic elastomeric olefin, copolyester, and styrenic thermoplastic elastomer, carbon fiber, glass fiber, ceramics, methacrylates, poly (N-isopropylacrylamide), PEO-PPO-PEO (pluronics), rubber, plastic, or combinations thereof.

It should be understood that the plurality of seals 125, 127, and 129 can be any member suitable for sealing a portion of the shaft 105. The positioning of the seals corresponds to the water and air channels. The seals serve to prevent air from entering the water channel and to prevent air from exiting anywhere other than outside of the vent hold on the top of the shaft 105. In some embodiments, the plurality of seals can be permanently attached to the shaft 105, such as for example, by over-molding. In other embodiments, the plurality of seals can be removably attached to the shaft 105, such as for example, by sliding the seal onto shaft 105. Like other components of the air/water valve 100, the plurality of seals can comprise polyurethane, polyurea, polyether(amide), PEBA, thermoplastic elastomeric olefin, copolyester, and styrenic thermoplastic elastomer, carbon fiber, glass fiber, ceramics, methacrylates, poly (N-isopropylacrylamide), PEO-PPO-PEO (pluronics), rubber, plastic (e.g., polycarbonates), ABS, MABS, silicone or combinations thereof.

In embodiments, the air/water valve 100, when attached to or mounted onto an endoscope enables an air-flow rate of at least 800 cc/min from the tip section of the endoscope, wherein the tip section is capable of an overall output of about 1500 cc/min at a pressure of 0.05 MPa (mega pascal). In some embodiments, the seal 127 is fabricated from a TPE (Thermoplastic Elastomer) material having a wall thickness of 0.35 mm and a 50 shore A hardness which enables an air-flow rate of at least 800 cc/min. In a preferred embodiment, the seal 127 is fabricated from a TPE material having a wall thickness of 0.22 mm and a 50 shore A hardness which enables an air-flow rate in a range of 1250 to 1300 cc/min. It should be appreciated that the wall thickness for the seal 127 may vary, in other embodiments, depending upon at least the type of material, hardness, geometry, molding conditions and number of support ribs. In some embodiments, the seal 127 includes, along its sides, a plurality of ribs. One embodiment of the seal 127 comprises four ribs 90 degrees apart from one another—two fully spanning the cross-section of the seal and the other two acting as filling channels. In one embodiment, the air-flow rate is a minimum of 700 cc per minute.

The shaft 105 provides an opening 155 and a passage or bore 160 that runs upwards through the shaft 105, substantially along a longitudinal axis 170, from the opening 155 to an end or vent 165. The opening 155 lies along an axis 172 that is substantially perpendicular to the longitudinal axis 170. When the end or vent 165 is not covered by an operator, air may travel via the opening 155 and up the passage or bore 160 to escape from the vent 165.

The inner ring 135 has a diaphragm or collar 136 extending from an outer circumference of the inner ring 135 to the internal circumference of the outer cap 140. The resilient member 145 is installed to lie between the inner ring 135 and the button cap 150 such that one end of the resilient member 145 is secured to the diaphragm or collar 136 and the other end to the button cap 150. In some embodiments, the inner ring 135 is a monolithic internally molded part of the outer cap 140 while in other embodiments these may be two separate components. In various embodiments, the outer cap 140 (along with the inner ring 135 when molded as a monolithic part of the outer cap 140) is molded using material of sufficient rigidity. In an embodiment, the outer cap 140 is molded from ABS having a Rockwell R hardness of 112 or hardness in the range of 70 to 90 shore D. The inner ring 135, outer cap 140 and the button cap 150 respectively define internal bores for receiving the end or vent 165 of the shaft 105. End 165 of the shaft 105 is placed through inner ring 135 and resilient member 145 and secured to the button cap 150 (as shown in FIGS. 1C, 1D). When assembled, the diaphragm or collar 136 of the inner ring 135 rests upon the ridge 123.

In accordance with an aspect of the present specification and as shown in FIG. 1D, an internal ring 180 of the button cap 150 is secured to the shaft 105, at the end 165, within a tapered notch, groove or recessed portion 175 (on the outer diameter of the shaft 105) defined between a detent or protrusion 178 (towards the end 165) and a ridge 179. In an embodiment, the notch portion 175 is tapered at an angle 'A' with reference to a vertical line parallel to the longitudinal axis 170.

Conventional valves typically use adhesive or welded joints to join or secure the button cap to the shaft. However, the securing mechanism of the present specification allows the use of dissimilar materials for the components such as the button cap 150 and the shaft 105. For example, the shaft 105 may be of metal while the button cap 150 may be of plastic or the shaft 105 and the button cap 150 may both be of plastic yet of different melt temperatures. During a sterilization process, such as autoclaving, the plastic button cap 150 will melt and then become secured to shaft 105 as it dries post sterilization. Using dissimilar material for the button cap 150 and shaft 105 eliminates the need of matching material properties required in a gluing or welding process. Typically, materials must be selected so that they have similar melt temperatures (in the case of welding) or have surface properties conducive to adhesives. Eliminating such constraints allows the individual component materials of the button cap 150 and shaft 105 to be optimized for their specific purposes. For example, in some embodiments, the button cap is molded out of a lubricious plastic (ABS, Acetal, PTFE) that is cheap to manufacture. In some embodiments, the shaft 105 is machined out of steel and mechanically bonded to a plastic button. Use of a machined steel shaft allows for dimensional and geometric tolerances (diameter, straightness) that are difficult or impossible to meet with conventional molding. The shaft 105 and the button cap 150, though manufactured of different materials or materials of different properties may be easily secured using the securing mechanism of the present specification. This further allows for optimization of materials for the shaft 105 and the button cap 150 and therefore the fabrication, manufacturing and assembly processes.

In accordance with another aspect of the present specification and as shown in FIGS. 1C, 1E and 1F, a plurality of hinges or hooks 182 extend vertically downwards (substantially parallel to the longitudinal axis 170) from the diaphragm or collar 136. The plurality of hinges 182 enables attachment of the air/water valve 100 to a corresponding mount of an endoscope. In various embodiments, the corresponding mount of an endoscope comprises a flange which is surrounded by ribs 185 of the outer cap 140, as described further below, and onto which the hinges 182 of the outer cap 140 snap and connect. Thus, ribs 185 and hinges 182 contained within outer cap 140 are used to connect the air/water valve to the flange of an endoscope. In various embodiments, the flange is an integral part of the endoscope and not single use or disposable. Use of the hinges 182 for attachment prevents vertical displacement of the seals and provides an audible and tactile positive locking 'snap' indicating to a user that the valve 100 is properly seated. Conventionally, over-molded TPE/TPU/Silicone in a two-part design is used for attaching the valve to the endoscope mount. However, the attachment mechanism enabled by the plurality of hinges 182 of the present specification is easier to manufacture while also providing a more secure connection to the endoscope during use. Specifically, inclusion of the hinges 182 reduces the overall part count. A single component is molded for the device of the present specification, whereas, in the prior art, a two-step molding process must be used or manual assembly of a rubber boot with a rigid plastic collar is required. A single mold results in shorter molding times and lower tooling costs. Elimination of a manual assembly step reduces overall labor input into the device.

In accordance with aspects of the present specification, it is desirable to configure or design the hinges or hooks 182 so that it achieves both a tactile, locking feel while the valve 100 is attached to the endoscope mount (using the hinges 182) but is not so engaged that removing the valve 100 (such as for autoclaving, for example) poses a challenge. In other words, it is desired that the amount of insertion force required to engage the hinges or hooks 182 to the endoscope mount should be optimal that enables sufficient retention or attachment of the valve 100 to the endoscope mount without the retention being too strong to enable detachment of the valve 100 from the endoscope mount a challenge.

FIGS. 1G through 1J, respectively illustrate first, second, third and fourth hinges or hooks 182g, 182h, 182i, 182j configured in accordance with various embodiments. In various embodiments, each hinge or hook 182g, 182h, 182i, 182j respectively comprises a barb 191, 192, 193, 194 which is curved or angled (lead-in angle) on at least a portion and a tine 195, 196, 197, 198, which is a straight portion. Together, the barb and tine form an opening that is used to attach the valve 100 to an endoscope mount 101. In an embodiment, the barb faces an inner diameter of the valve and the tine faces the outer diameter of the valve. In embodiments, the amount of insertion force required to engage a valve with an endoscope mount, degree of retention of the mounted valve, amount of depression force required to actuate the mounted valve and the amount of removal force required to disengage the valve from the endoscope mount are determined by at least a width 'w' and a lead-in angle θ of the barb.

In one embodiment, as shown in FIG. 1G, the barb 191 has a width $w_g=0.5$ mm and a lead-in angle $\theta_g=45$ degrees enabling the hinge or hook 182g to require a first amount of insertion/removal force.

In another embodiment, as shown in FIG. 1H, the barb 192 has a width $w_h=0.25$ mm and a compound lead-in angle $\theta_h=45/15$ degrees (different lead-in angles for each side) enabling the hinge or hook 182h to require a second amount of insertion/removal force.

In another embodiment, as shown in FIG. 1I, the barb 193 has a width $w_i=0.5$ mm and a compound lead-in angle $\theta_i=45/15$ degrees (different lead-in angles for each side) enabling the hinge or hook 182i to require a third amount of insertion/removal force.

In yet another embodiment, as shown in FIG. 1J, the barb 194 has a width $w_j=0.5$ mm and a lead-in angle $\theta_j=15$ degrees enabling the hinge or hook 182j to require a fourth amount of insertion/removal force.

The amount of insertion/removal force corresponding to the hinges or hooks 182g through 182j varies as follows: first insertion/removal force>second insertion/removal force>third insertion/removal force>fourth insertion/removal force. Accordingly, the corresponding retention is highest for hinge or hook 182g progressively reducing for hinges or hooks 182h, 182i and lowest for hinge or hook 182j. Therefore, it can be generalized that the greater the width and the greater the compound lead-in angle, the greater the amount of force needed for insertion/removal.

As an example, air/water valve hinges or hooks having barb dimensions of 140 microns, 70 microns and 35 microns were tested to determine insertion force, removal force, and depression force. Note that a unit having 0 microns (or no barb) would have a very low retention force that would be insufficient for the purposes of the present invention. As shown in the table 205 in FIG. 2A, for the 140 micron hooks, the insertion force varied from 8.1 to 12.2 N. As shown in table 210 in FIG. 2B, for the 70 micron hooks, the insertion force varied from 7.4 to 13N. As shown in table 215 in FIG. 2B, for the 35 micron hooks, the insertion force varied from 6.4 to 12N. While there is some overlap, the general trend shows that the thinner the barb, the less the insertion force required.

As shown in the table 220 in FIG. 2D, for the 140 micron hooks, the removal force varied from 5.8 to 14.2 N. As shown in the table 225 in FIG. 2E, for the 70 micron hooks, the removal force varied from 4.0 to 9.2 N. As shown in the table 230 in FIG. 2F, for the 35 micron hooks, the removal force varied from 4.5 to 6.6 N. Again, while there is some overlap, the general trend shows that the thinner the barb, the less the removal force required.

Figure 3A:
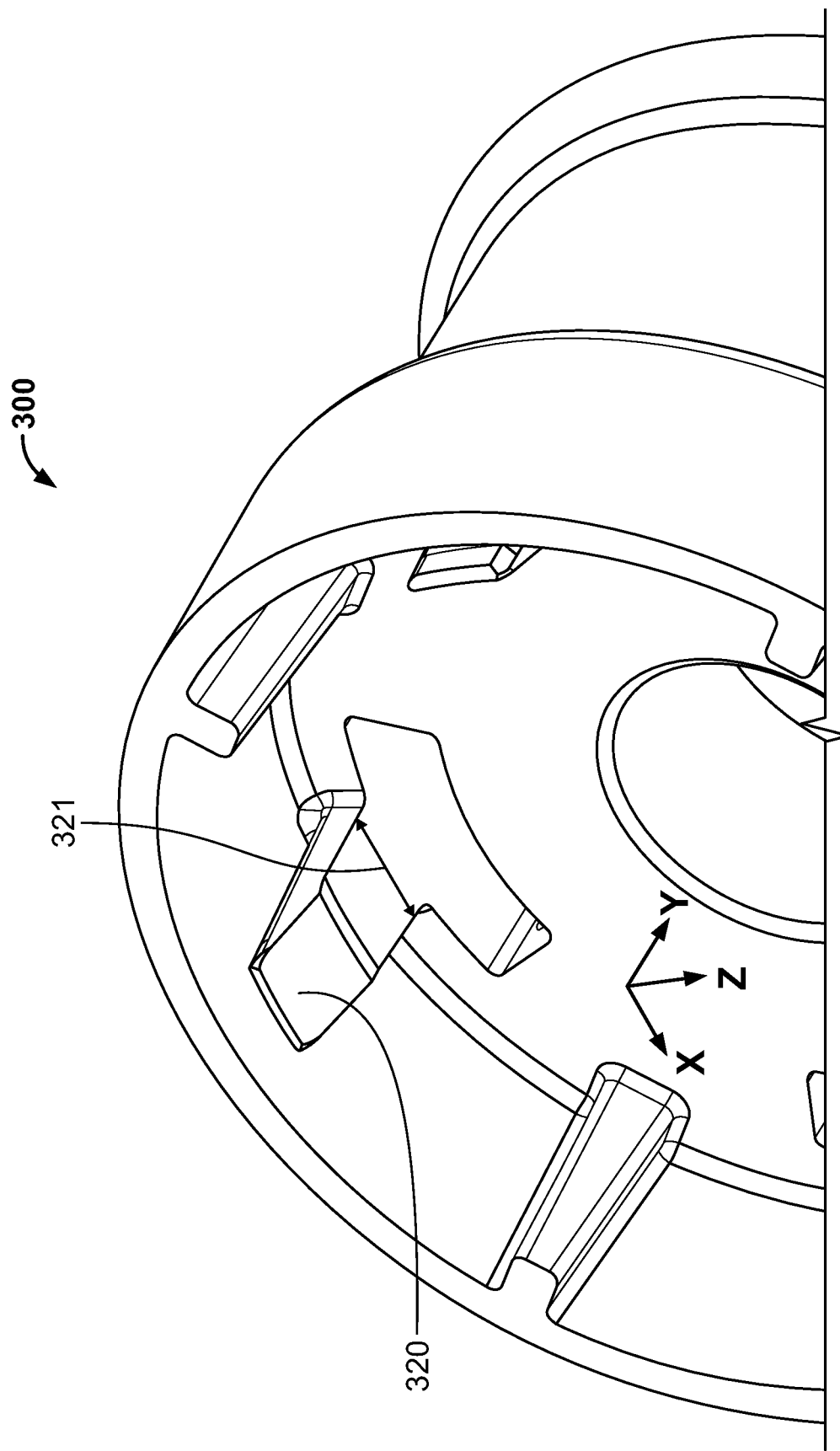
FIG. 3A is an illustration showing various dimensions of a 70 micron hook that is used in an air/water valve of the present specification.
Figure 3B:
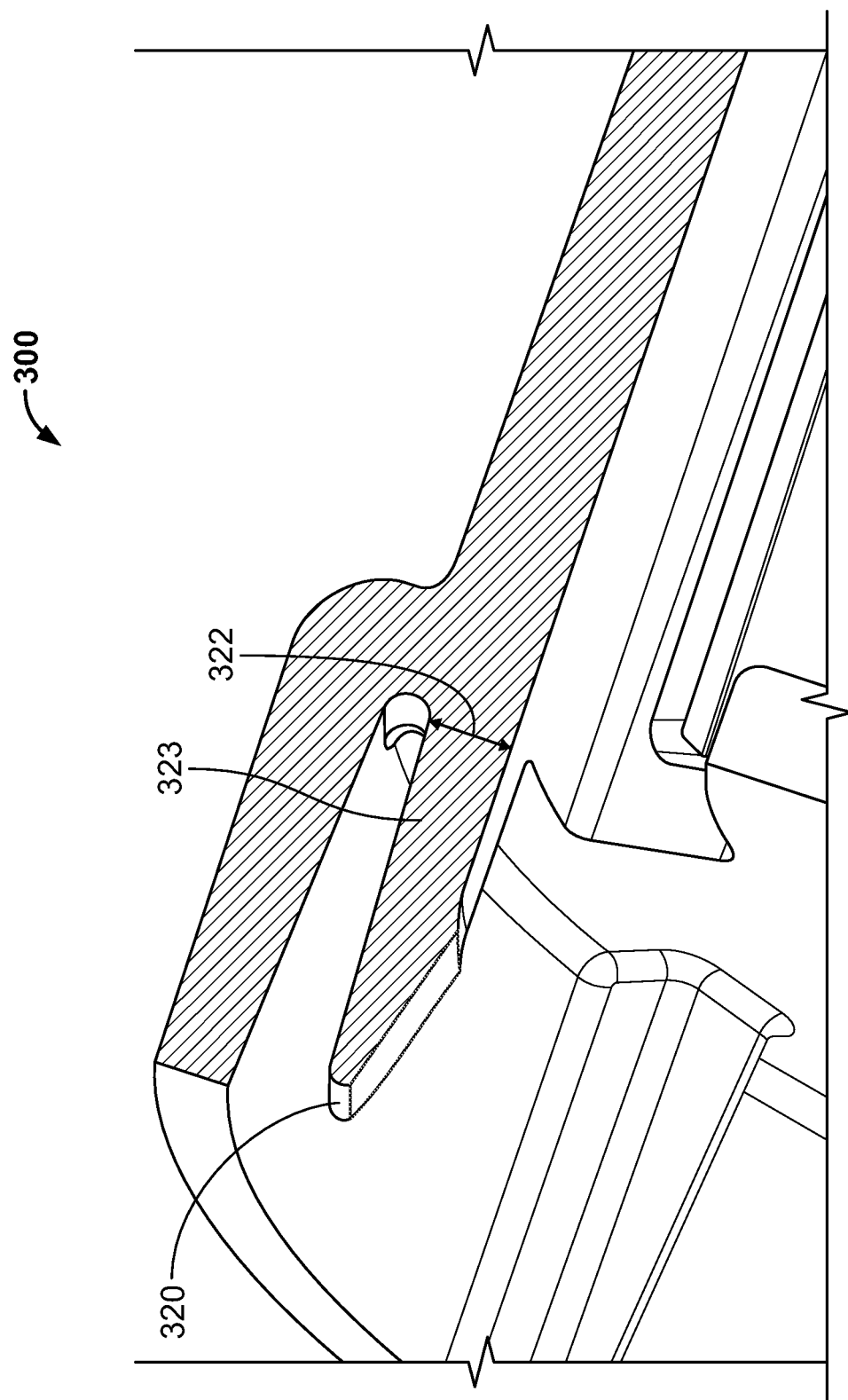
FIG. 3B is an illustration showing various dimensions of a 70 micron hook that is used in an air/water valve of the present specification.
Figure 3C:
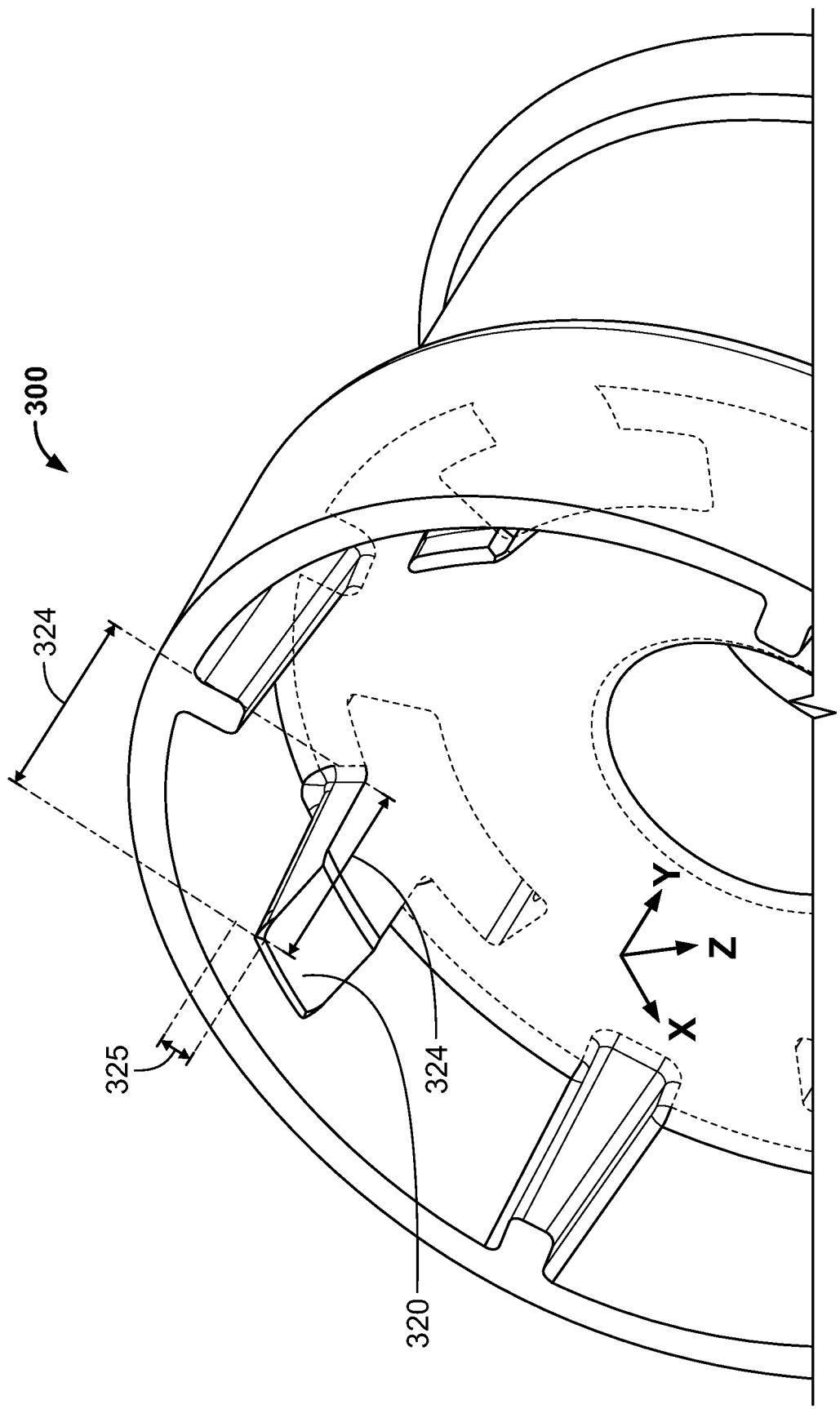
FIG. 3C is an illustration showing various dimensions of a 70 micron hook that is used in an air/water valve of the present specification.

FIGS. 3A, 3B and 3C are partial diagrams of a molded and machined air/water outer cap 300. In an embodiment, as shown in FIG. 3A, an exemplary molded hook portion 320 has a width 321 of approximately 2.10 mm. Further, as shown in FIG. 3B, the thickness 322 of the hook 320 at a base portion 323 is approximately 0.7 mm. In an embodiment, it should be noted that the thickness 322 of the base portion 323 of the hook 320 ranges from 0.5 mm to 1.0 mm, as too thick of a hook will lead to stiffness and too thin of a hook will lead to a part that is not moldable.

As shown in FIG. 3C, the overall length or height 324 of the hook 320 is approximately 3.8 mm. Further, hook 320 travels a distance 325 of 0.504 mm when depressed or engaged. As shown in the table 314 in FIG. 3D, for the 140 micron hooks, the depression force varied from 9.15 to 20.95 N. As shown in the table 316 in FIG. 3E, for the 70 micron hooks, the depression force varied from 9.40 to 18.94 N. As shown in the table 318 in FIG. 3F, for the 35 micron hooks, the depression force varied from 10.65 to 15.26 N. Again, while there is some overlap, the general trend shows that the thinner the barb, the less the depression force required.

In one embodiment, the hook, having a barb and tine, comprises a barb having a width of less than 200 micron.

In accordance with still another aspect of the present specification and as shown in FIGS. 1E and 1F, a plurality of positioning ribs 185 are formed along the inner circumference of the outer cap 140. The ribs 185 extend vertically downwards (substantially parallel to the longitudinal axis 170) along the inner circumference of the outer cap 140. The ribs 185 enable the valve 100 to be centered on a valve well on the endoscope, aligning the shaft 105 with a center of the valve well and enabling precise vertical positioning of the plurality of seals within the valve well. The ribs 185 act as edge stops to ensure the valve 100 is centered on the mount and also prevent side loading from the user from breaking the seals on the valves.

In various embodiments, the shaft 105 of the disposable air/water valve 100 along with the plurality of ridges and grooves are of the same material as the shaft 105. Similarly, the plurality of hinges or hooks 182 and ribs 185 may be molded as components of the inner ring 135 and the outer cap 140 (the inner ring 135 and outer cap 140 may also be molded as a single component) in accordance with various embodiments. It should be appreciated that the shaft 105, the plurality of seals 125, 127, and 129, inner ring 135, outer cap 140 and button cap 150 may all be manufactured from dissimilar materials and still be easily assembled or secured together in accordance with various aspects of the present specification.

Figure 4B:
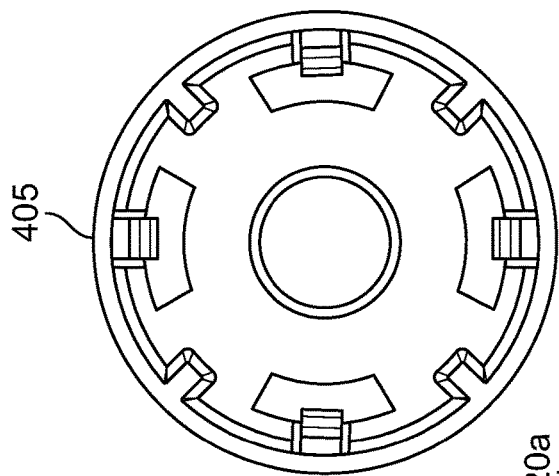
FIG. 4B shows a bottom view (or attachment portion) of the outer cap of FIG. 4A that is used to attach the air/water valve to a corresponding mount of an endoscope.
Figure 4D:
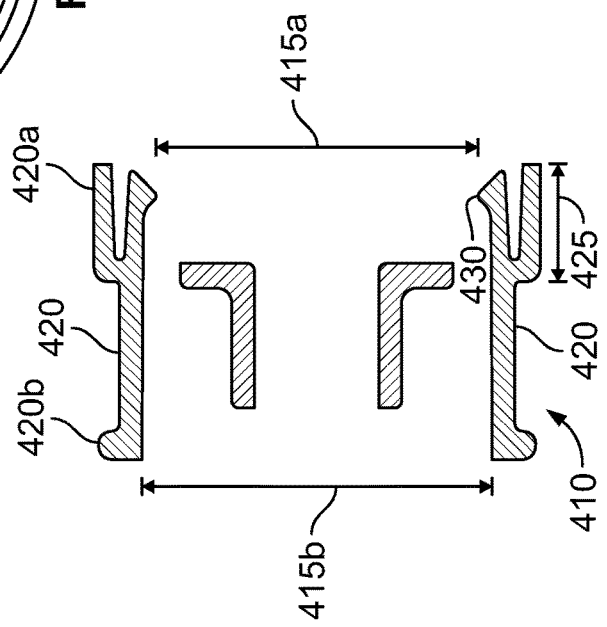
FIG. 4D is a cross-sectional view of the outer cap of FIG. 4C.
Figure 4A:
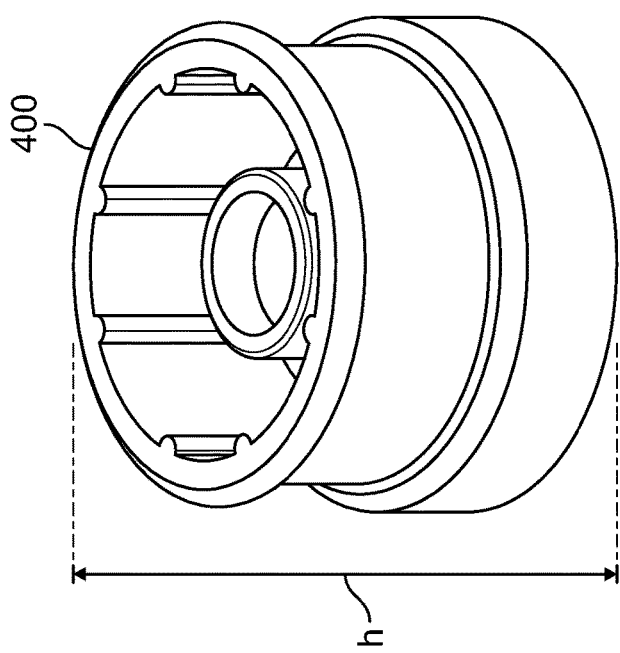
FIG. 4A illustrates an embodiment of an exemplary outer cap with a hook size of 70 micros and a lead-in angle of 15 degrees on each side.
Figure 4C:
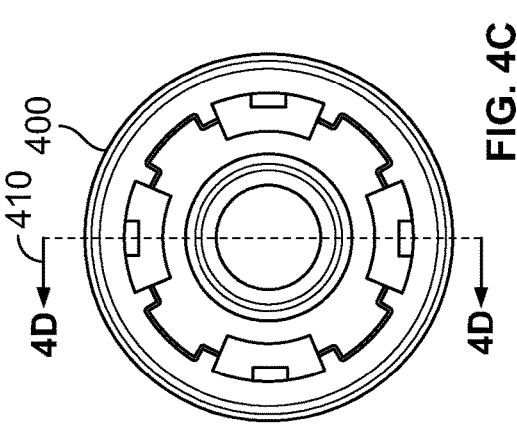
FIG. 4C is a diagram showing the location of cross-section A-A of an outer cap.

As described with respect to FIGS. 1C, 1E and 1F, a plurality of hinges or hooks 182 extend vertically downwards (substantially parallel to the longitudinal axis 170) from the diaphragm or collar 136. The plurality of hinges or hooks 182 enables attachment of the air/water valve 100 to a corresponding mount of an endoscope. FIGS. 4A, 4B, 4C, 4D, 4E, 4F, and 4G illustrate an exemplary outer cap and associated components having a barb hook size of 70 microns with a lead-in angle of 15 degrees on each side. Outer cap 500 is shown in FIG. 4A and in an embodiment, has a height 'h' of approximately 12.20 mm. FIG. 4B shows the underside 405 or attachment portion of outer cap 400 that is used to attach the air/water valve to a corresponding mount of an endoscope. As shown in FIG. 4B, the attachment portion 405 may have a diameter of approximately 18.33 mm. FIG. 4C is a diagram showing the cross-section A-A 410 of outer cap 400 which is described in greater detail in FIG. 4D. As shown in FIG. 4D, cross section A-A 410 of the outer cap 400 shows an approximate distance 415a of 13.30 mm between hooks 420, at a proximal end 420a, at the barbs 430 where the hook engages with a flange on the corresponding mount of an endoscope. At a distal end 420b, the approximate distance 415b between hooks 420 is 14.50 mm. Further, the approximate length 425 of each hook 420 is 4.10 mm.

Figure 4E:
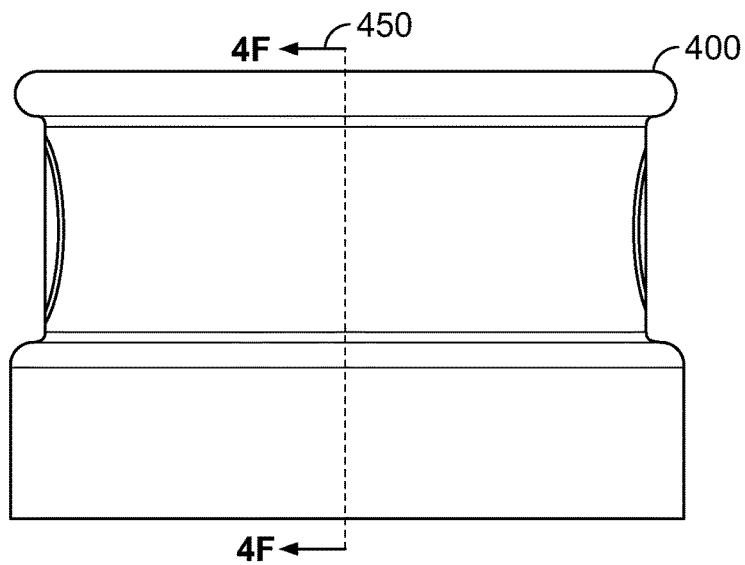
FIG. 4E is a diagram showing the location of cross-section A-A on an outer cap.
Figure 4F:
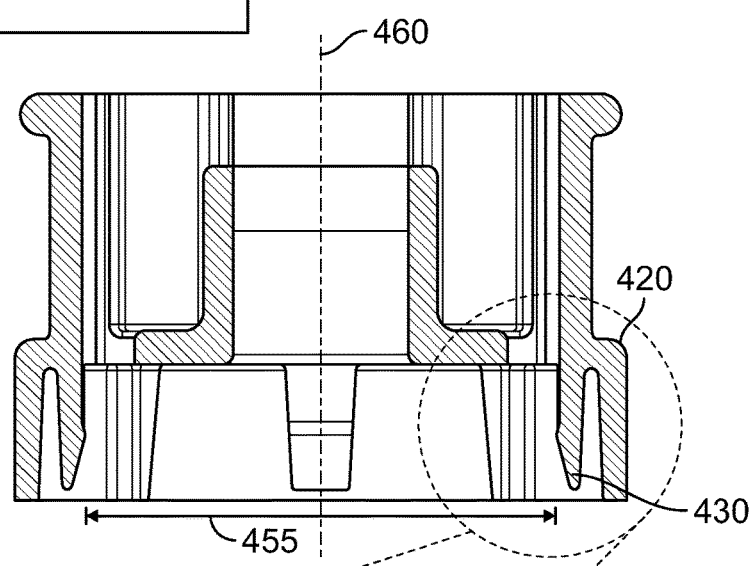
FIG. 4F is a cross-sectional view of the outer cap of FIG. 4E.
Figure 4G:
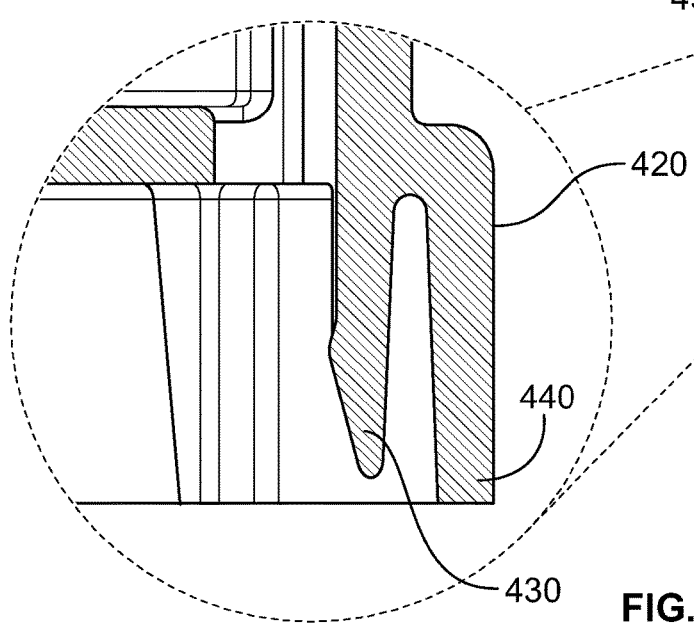
FIG. 4G which represents an exploded view of cross section B-B of FIG. 4F.

FIG. 4E shows outer cap 400 with cross-section A-A 450 in a different view, as represented by FIG. 4F. As shown in FIG. 4F, the approximate distance 455 between barbs 430 of the hook 420 (where the hook engages with a flange on the corresponding mount of an endoscope) is 14.185±0.06 mm. In one embodiment, the barbs 430 are machined at an angle 435 of approximately 15±3 degrees with respect to a central longitudinal axis 460. Further, a straight edge of barbs 430, located just above the angular slanted portion, is machined at a distance of approximately 7.530 mm from the central longitudinal axis 460. This detail is shown in FIG. 4G which represents an exploded view of cross section B-B of FIG. 4F. Further, a straight portion or tine 440 of hook 420 extends approximately 0.320±0.1 farther than barbs 430.

Figure 5:
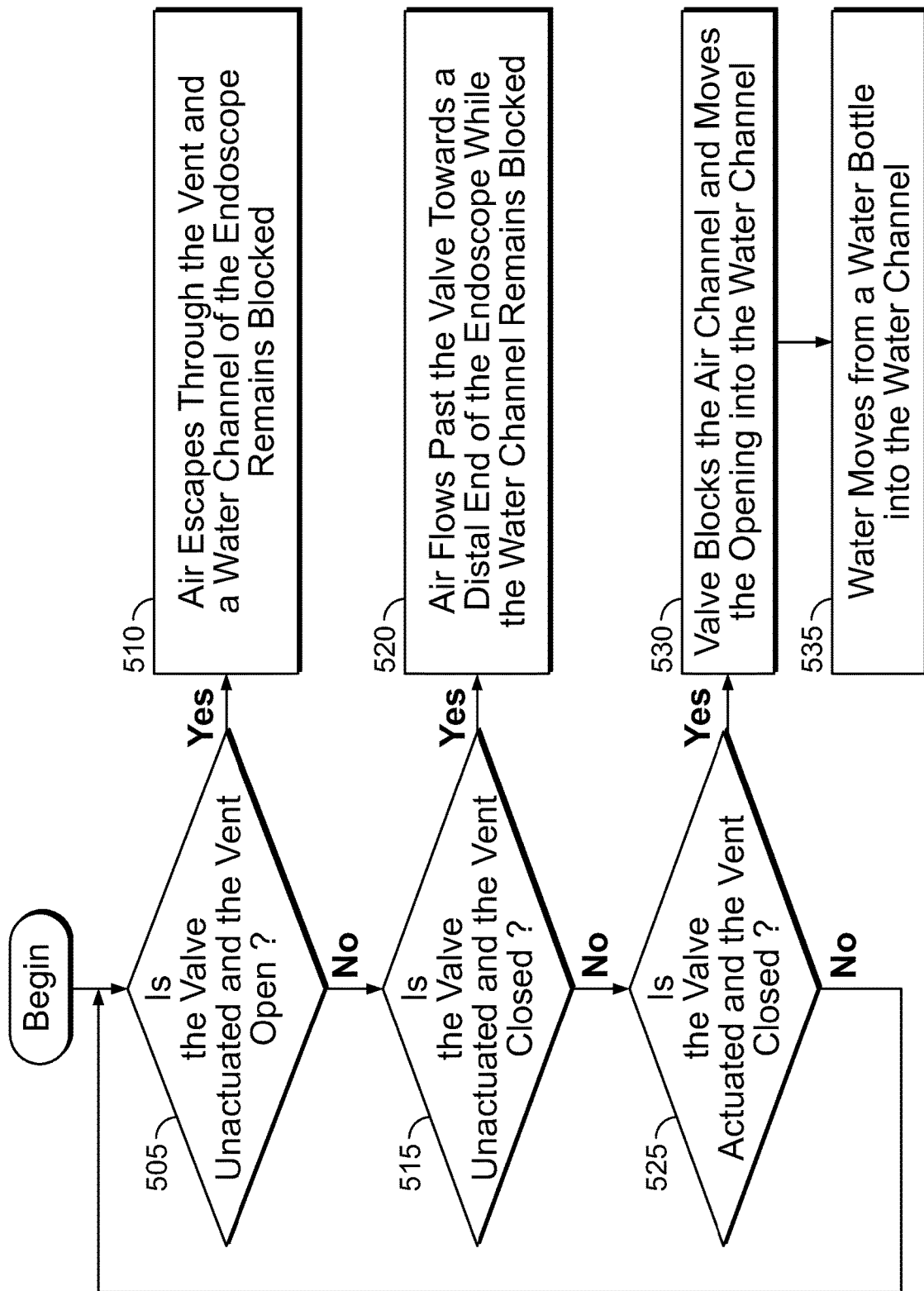
FIG. 5 is a flow chart illustrating a plurality of exemplary steps involved in operating an air/water valve of the present specification.

FIG. 5 is a flow chart illustrating a plurality of exemplary steps involved in operating an air/water valve of the present specification. Referring now to FIGS. 1A through 1D and FIG. 5, during operation the air/water valve 100 of the present specification may be positioned in an air/water cylinder of an endoscope. The endoscope provides an air channel for air and a water channel for water. The air and water channels are connected to a water bottle. The water channel extends into the fluid contained in the water bottle. When air/water valve 100 is placed in the air/water cylinder of the endoscope, the air/water valve 100 passes through both the air and water channels.

At step 505, the air/water valve 100 is un-actuated, that is the button cap 150 is not depressed and the resilient member 145 is not compressed, and the vent 165 is open. As a result, at step 510 the air/water valve 100 allows air flow (provided by an air pump, for example) to enter the valve opening 155 and escape from the vent 165. Note that disposable air/water valve 100 provides a plurality of seals (125, 127, and 129) that prevent air or water from leaking from the air or water channels. Also, the opening 155 of the air-water valve 100 is not aligned with the water channel and therefore there is no movement of water away from the water bottle, as the water channel is blocked.

At step 515, the air/water valve 100 is unactuated, that is the button cap 150 is not depressed and the resilient member 145 is not compressed, but the vent 165 is closed or covered by an operator (using his finger, for example). As before, from the previous step 510, the water channel is still blocked by the air/water valve 100. Since the air vent 165 is now blocked by the operator, air from the air pump flows, at step 520, past the air/water valve 100 towards a distal end of an endoscope. This allows the operator to insufflate a body cavity by blocking the air vent 165 of air/water valve 100 without actuating the valve.

At step 525, the air/water valve 100 is actuated, that is the button cap 150 is depressed and the resilient member 145 is compressed, and the vent 165 continues to remain obstructed, closed or covered by the operator. Depressing the button cap 150 causes a downward force to be applied to the shaft 105 via ridge 179 and therefore the shaft 105 moves or is displaced downwards. Also, depressing the button cap 150 causes the resilient member 145 to compress against the supporting collar or diaphragm 136.

The collar 136 rests against the endoscope mount and is therefore prevented from moving downwards (due to the depression of the button cap 150). The downward movement or displacement of the shaft 105 causes the valve 100 to block the air channel and moves the opening 155 into the water channel, thereby creating a passageway for water to pass through the air/water valve 100, at step 530. Because the vent 165 is also blocked by the operator pressing down on the valve 100 (for depressing the button cap 150), air flows instead into the water bottle via an air branched-channel connected to the water bottle. As the air pressure in water bottle increases, fluid is forced from the water bottle into the water channel, at step 535. Thus, by actuating the air/water valve 100, the operator causes water to flow towards the distal end of the endoscope for rinsing or irrigation.

When the operator stops depressing the button cap 150, the compressed resilient member 145 begins to recoil or get uncompressed. The recoiling resilient member 145 applies an upward force to the button cap 150 that in turn transfers the upward force to the shaft 105 via the detent or protrusion 178. This causes both the shaft 105 and the button cap 150 to be displaced upwards and return to the un-actuated position of the valve 100 of step 505.

FIG. 6A is a perspective view of a disposable suction valve 600 in accordance with an embodiment of the present specification, FIG. 6B is a top view of the disposable suction valve 600, FIG. 6C is a vertical cross-section view along an axis F-F of the disposable suction valve 600 of FIG. 6A while FIG. 6D is a horizontal cross-section view along an axis G-G of the disposable suction valve 600 of FIG. 6C. Referring now to FIGS. 6A through 6D, the disposable suction valve 600 comprises a stem or shaft 605 of outer diameter 'D' and having a first groove or recess 610 (of a first diameter $d_1$) and a second groove or recess 612 (of a second diameter $d_2$) formed on the outer circumference of the shaft 605 and towards an end 615 of the shaft 605; the first and second grooves 610, 612 result in the formation of a first ridge 611 and a second ridge 613; an inner ring 620 having a bore of a first internal diameter $b_1$ along a first length $l_1$ (parallel to the longitudinal axis F-F) of the bore and a second internal diameter $b_2$ along a second length $l_2$ (parallel to the longitudinal axis F-F) of the bore, wherein $b_1$ is approximately equal to $d_2$ and $b_2$ is approximately equal to 'D'; an outer cap 630; a resilient member 635 such as, but not limited to, spring, rubber, elastic; and a button cap 640 having a central bore (along the longitudinal axis F-F).

The components of the disposable suction valve 600 may comprise disposable material, including, but not limited to polyurethane, polyurea, polyether(amide), PEBA, thermoplastic elastomeric olefin, copolyester, styrenic thermoplastic elastomer, carbon fiber, glass fiber, ceramics, methacrylates, poly (N-isopropylacrylamide), PEO-PPO-PEO (pluronics), rubber, plastic (e.g., polycarbonates), ABS, MABS, silicone, or combinations thereof. The resilient member 635 may be formed from a suitable material, such as corrosion resistant metal, polyurethane, polyurea, polyether(amide), PEBA, thermoplastic elastomeric olefin, copolyester, and styrenic thermoplastic elastomer, carbon fiber, glass fiber, ceramics, methacrylates, poly (N-isopropylacrylamide), PEO-PPO-PEO (pluronics), rubber, plastic, or combinations thereof.

The shaft 605 provides an opening 655 and a passage or bore 660 that runs through the shaft 605, substantially along the longitudinal axis F-F, from the opening 655 and vertically downwards to an end, opening or vent 665. The opening 655 lies along an axis G-G that is substantially perpendicular to the longitudinal axis 670. Fluid may pass horizontally through one side of the opening 655 and vertically downwards through the vent 665. Opening 655 and vent 665 allow air or fluid to pass through a suction channel of the endoscope when the suction valve 600 is actuated.

The inner ring 620 has a diaphragm or collar 625 (FIG. 6D) extending from an outer circumference of the inner ring 620 to the internal circumference of the outer cap 630. The resilient member 635 resides between the inner ring 620 and the button cap 640 such that one end of the resilient member 635 is secured to the diaphragm or collar 625 and the other end to the button cap 640. In some embodiments, the inner ring 620 is a monolithic internally molded part of the outer cap 630 while in other embodiments these may be two separate components. The inner ring 620, outer cap 630 and the button cap 640 respectively define internal bores for receiving the end 615 of the shaft 605. End 615 of the shaft 605 is placed through inner ring 620 and resilient member 635 and secured to the button cap 640. When assembled, the first length $l_1$ of the bore of the inner ring 620 fits over the second groove 612 (since, $b_1$ is approximately equal to $d_2$) to rest upon the second ridge 613.

In accordance with an aspect of the present specification and as shown in FIG. 6C, an internal ring 680 of the button cap 640 is secured to the shaft 605, at the end 615, within the first groove or recess 610 that has a taper defined between a detent or protrusion 678 (towards the end 615) and the first ridge 611. In an embodiment, the first groove or recess 610 is tapered at an angle 'N' with reference to a vertical line parallel to the longitudinal axis F-F. Conventional designs typically join or secure the button cap to the shaft using adhesive or welded joints. For optimal performance, the suction valve shaft requires a high degree of dimensional precision, generally not available to molded components. The securing mechanism of the present specification allows for a higher degree of dimensional precision through the use of dissimilar materials for the components such as the button cap 640 and the shaft 605. For example, the shaft 605 may be of metal while the button cap 640 may be of plastic or the shaft 605 and the button cap 640 may both be of plastic yet of different melt temperatures. During a sterilization process, such as autoclaving, the plastic button cap 640 will melt and then become secured to shaft 605 as it dries post sterilization. Using dissimilar material for the button cap 640 and shaft 605 eliminates the need of matching material properties required in a gluing or welding process. Typically, materials must be selected so that they have similar melt temperatures (in the case of welding) or have surface properties conducive to adhesives. Eliminating such constraints allows the individual component materials of the button cap 640 and shaft 605 to be optimized for their specific purposes. For example, in some embodiments, the button cap is molded out of a lubricious plastic (ABS, Acetal, PTFE) that is cheap to manufacture. In some embodiments, the shaft 605 is machined out of steel and mechanically bonded to a plastic button. Use of a machined steel shaft allows for dimensional and geometric tolerances (diameter, straightness) that are difficult or impossible to meet with conventional molding. The shaft 205 and the button cap 640 though manufactured of different materials or materials of different properties may be easily secured using the securing mechanism of the present specification. This further allows optimization of materials for the shaft 605 and the button cap 640 and therefore their manufacturing and assembling processes.

Figure 6E:
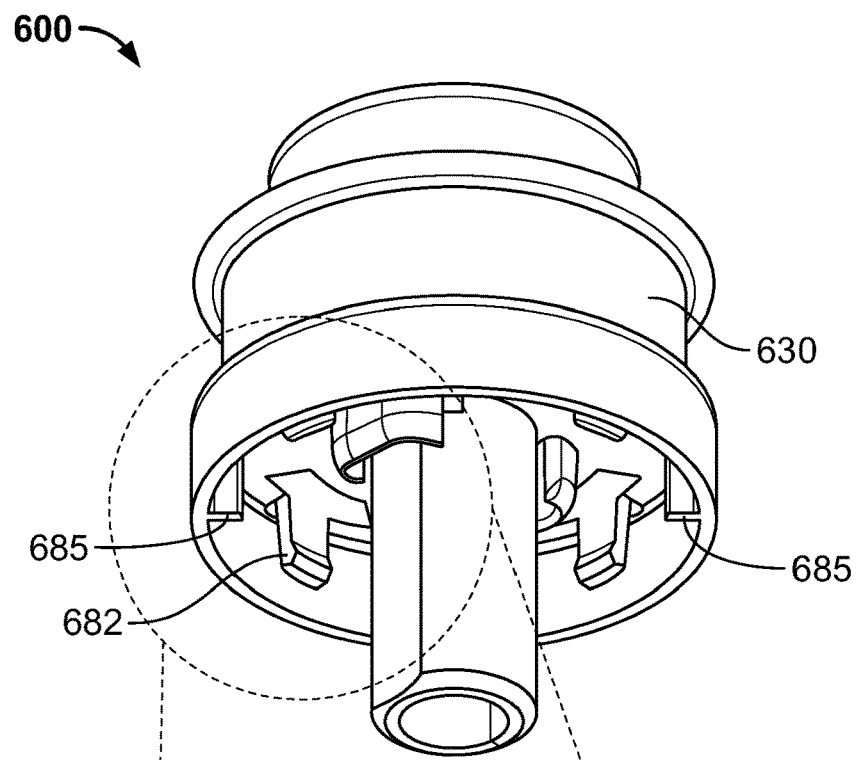
FIG. 6E is a bottom perspective view of the disposable suction valve of FIG. 6A.
Figure 6F:
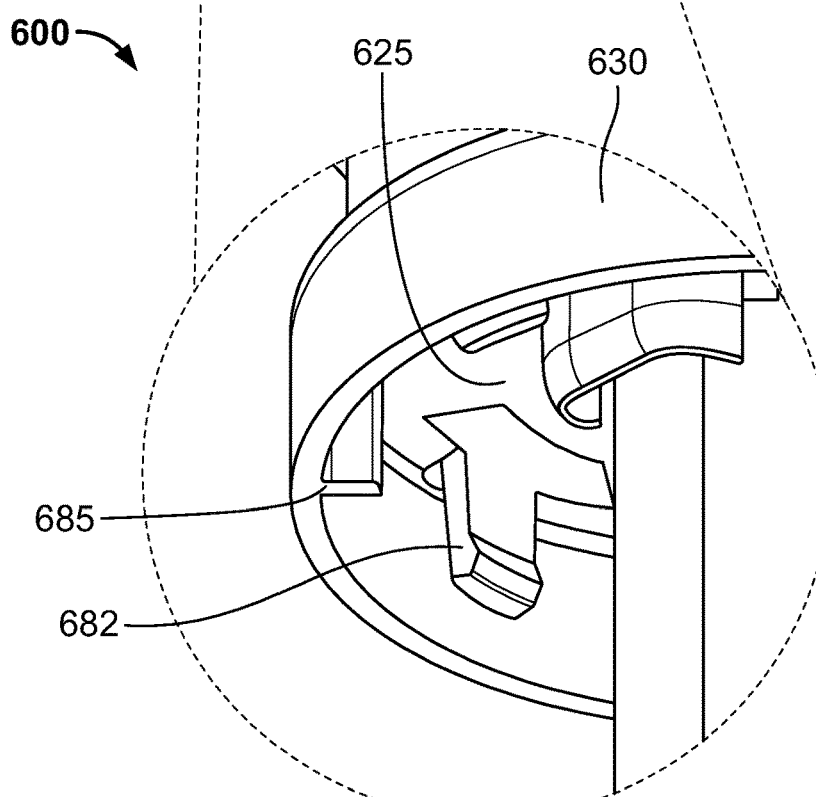
FIG. 6F is a magnified view of the bottom of the disposable suction valve of FIG. 62E; and, FIG. 7 is a flow chart illustrating a plurality of exemplary steps involved in operating a suction valve of the present specification.

In accordance with another aspect of the present specification and as shown in FIGS. 6D, 6E and 6F, a plurality of hinges or hooks 682 extend vertically downwards (substantially parallel to the longitudinal axis F-F) from the diaphragm or collar 625. The plurality of hinges or hooks 682 enables attachment of the suction valve 600 to a corresponding mount of the endoscope. In various embodiments, the corresponding mount of an endoscope comprises a flange which ribs 685 of the outer cap 630 surround, as described further below, and on to which the hinges 682 of the outer cap 630 snap and connect. In various embodiments, the flange is an integral part of the endoscope and not single use or disposable. The hinges or hooks 682 allow the collar component to be a single molded part, rather than an over-molded component or an assembly. Use of the hinges or hooks 682, for attachment, provides an audible and tactile positive locking 'snap' indicating to the user that the valve 600 is properly seated. Typically, a two-part over-molded TPE/TPU/Silicone design is used for attaching the valve to the endoscope mount. However, the attachment mechanism enabled by the plurality of hinges 682 of the present specification is easier to manufacture while also providing a more secure connection to the endoscope during use. Specifically, inclusion of the hinges 682 reduces the overall part count. A single component is molded for the device of the present specification, whereas, in the prior art, a two-step molding process must be used or manual assembly of a rubber boot with a rigid plastic collar is required. A single mold results in shorter molding times and lower tooling costs. Elimination of a manual assembly step reduces overall labor input into the device.

In accordance with still another aspect of the present specification and as shown in FIGS. 6D, 6E and 6F, a plurality of positioning ribs 685 are formed along the inner circumference of the outer cap 630. The ribs 685 extend vertically downwards (substantially parallel to the longitudinal axis F-F) along the inner circumference of the outer cap 630. The ribs 685 enable the valve 600 to be centered on a valve well on the endoscope, aligning the shaft 605 with a center of the valve well. The ribs 685 act as edge stops to ensure the valve 600 is centered on the mount.

In various embodiments, the plurality of hinges or hooks 682 and ribs 685 may be molded as components of the inner ring 620 and the outer cap 630 (the inner ring 620 and outer cap 630 may also be molded as a single component) in accordance with some embodiments. It should be appreciated that the shaft 605, inner ring 620, outer cap 630 and button cap 640 may all be manufactured from dissimilar materials and still be easily assembled or secured together in accordance with various aspects of the present specification.

Figure 7:
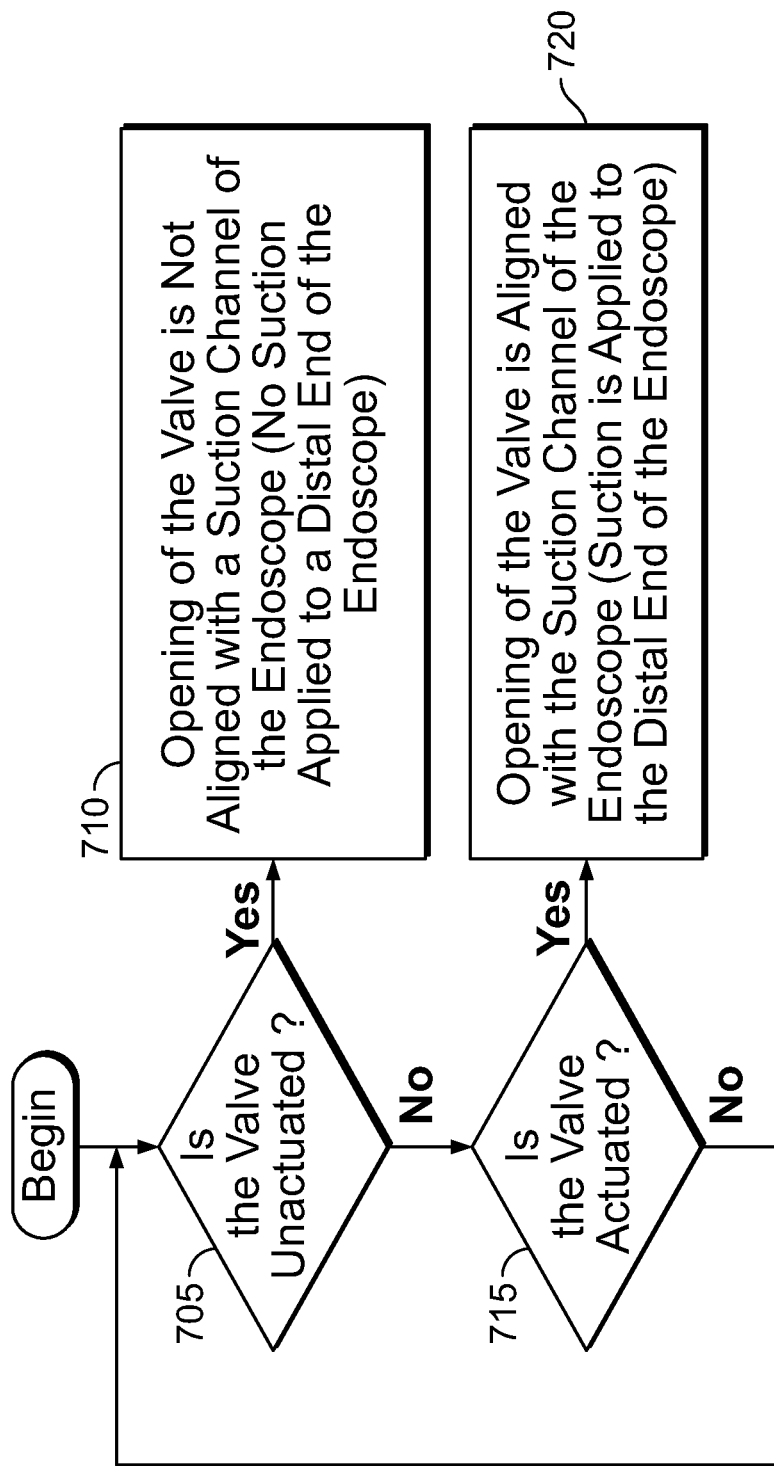

FIG. 7 is a flow chart illustrating a plurality of exemplary steps involved in operating a suction valve of the present specification. Referring now to FIGS. 6A through 6F and FIG. 7, during operation the disposable suction valve 600 of the present specification may be placed into a suction cylinder of the endoscope. A suction channel of the endoscope is linked to the opening 655 (of the suction valve 600) and leads to a distal end of an endoscope or leads toward the patient. The endoscope may be connected to a suction pump to create negative pressure in the suction channel when the suction valve 600 is actuated.

At step 705, the suction valve 600 is unactuated, meaning that the button cap 640 is not depressed and the resilient member 635 is not compressed. As a result, at step 710, the opening 655 remains out of position with the suction channel of the endoscope, thereby preventing the suction pump from creating negative pressure in the suction channel (that is, no suction is applied to the distal end of the endoscope).

At step 715, the suction valve 600 is actuated—that is, the button cap 640 is depressed and the resilient member 635 is compressed. Depressing the button cap 640 causes a downward force to be applied to the shaft 605 via the first ridge 611 and therefore the shaft 605 moves or is displaced downwards. Also, depressing the button cap 640 causes compression of the resilient member 635 against the supporting collar or diaphragm 625. The ring 620 rests against the second ridge 613 as a result of which the collar 625 is prevented from moving downwards (due to the depression of the button cap 640). The downward movement or displacement of the shaft 605 causes the opening 655 to move into position with the suction channel from the distal end of the endoscope or from the patient. At step 720, by aligning the opening 655 with the suction channel of the endoscope, a negative pressure created by the suction pump cause flow from the distal end of the endoscope towards the opening 655 (that is, suction is applied to the distal end of the endoscope). As a result, air and/or fluid may be suctioned from the distal end of the endoscope when the disposable suction valve 600 is in an actuated position.

When the suction valve 600 is released—that is, button cap 640 is not depressed the resilient member 635 recoils and applies an upward force to the button cap 640 that in turn transfers the upward force to the shaft 605 via the detent or protrusion 678. This causes both the shaft 605 and the button cap 640 to be displaced upwards and return to the unactuated position of the valve 600 of step 705.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. A suction valve for a medical device, the suction valve comprising:
   a shaft having a longitudinal axis and a passage from a first opening to a vent;
   an outer cap comprising an inner ring, a diaphragm, and at least one hinge as molded parts of the outer cap, the diaphragm extending from an outer circumference of the inner ring to an internal circumference of the outer cap, wherein the at least one hinge extends downward from said diaphragm;
   wherein the at least one hinge is positioned radially outward, relative to the longitudinal axis, of the inner ring, and a portion of the outer cap is (i) distal of the hinge and (ii) radially outward, relative to the longitudinal axis, of the at least one hinge;
   a button cap attached to the shaft; and
   wherein a portion of the outer cap is radially outward, relative to the longitudinal axis, from the at least one hinge, and the at least one hinge is radially outward, relative to the longitudinal axis, from the inner ring; and
   wherein the at least one hinge is configured to couple the suction valve to a port of the medical device to prevent vertical displacement of a portion of the suction valve.

2. The suction valve of claim 1, wherein the button cap includes an internal ring, and the internal ring couples to the shaft by fitting into a tapered notch near the vent of the shaft.

3. The suction valve of claim 1, wherein each of the at least one hinge comprises a tine and a barb.

4. The suction valve of claim 3, wherein the barb is defined by a width of less than 200 microns.

5. The suction valve of claim 1, wherein the at least one hinge is configured to connect to a corresponding mount on the medical device.

6. The suction valve of claim 5, wherein each of the at least one hinge is configured to generate an audible and/or tactile snap when the at least one hinge connects to the corresponding mount.

7. The suction valve of claim 5, further comprising at least one rib positioned along the internal circumference of the outer cap, wherein each of the at least one rib is configured to center the suction valve on the mount.

8. The suction valve of claim 7, wherein the at least one rib is positioned at a distalmost portion of the outer cap.

9. The suction valve of claim 8, wherein each of the at least one rib extends inward from the internal circumference of the outer cap towards a central longitudinal axis of the shaft, is spaced from the shaft, and is configured to act as a stop to center the suction valve on the port.

10. A suction valve for a medical device, the suction valve comprising:
    a shaft having a passage from a first opening to a vent;
    an outer cap comprising an inner ring, a diaphragm, and at least one hinge as molded parts of the outer cap, the diaphragm extending radially outward to an inner surface of the outer cap, the at least one hinge extending downward from the diaphragm and configured to couple the suction valve to a port of the medical device to prevent vertical displacement of a portion of the suction valve, wherein a portion of the outer cap is radially outward and spaced from the at least one hinge;

a button cap fixed to the shaft; and a resilient member disposed between the button cap and the inner ring.

11. The suction valve of claim 10, wherein the at least one hinge extends downward from the inner ring, a plurality of vertical ribs extend along the inner surface of the outer cap, and the inner ring defines a central bore to accommodate the shaft.

12. The suction valve of claim 10, wherein the shaft has at least one groove, at least one ridge, and a protrusion formed at the vent.

13. The suction valve of claim 10, wherein the inner ring attaches to the shaft by engaging a tapered notch of the shaft.

14. The suction valve of claim 10, wherein the at least one hinge comprises a tine and a barb.

15. The suction valve of claim 10, wherein the resilient member includes a spring.

16. The suction valve of claim 10, wherein the at least one hinge is configured to generate an audible snap and/or a tactile snap when the hinge connects to the port.

17. The suction valve of claim 11, wherein each of the plurality of vertical ribs is configured to center the valve on the port.

18. A suction valve for a medical device, the suction valve comprising:

a shaft having a passage from a first opening to a second opening;

an outer cap comprising an inner ring, a diaphragm, and a hinge as molded parts of the outer cap, the diaphragm extending radially outward to an inner surface of the outer cap, the hinge extending downward from the diaphragm, wherein the hinge is spaced from the shaft and the hinge is configured to couple the suction valve to a port of the medical device to prevent vertical displacement of a portion of the suction valve;

a button cap having an internal ring coupled to the shaft; and a resilient member disposed between the button cap and the inner ring.

19. The suction valve of claim 18, wherein a portion of the outer cap is radially outward, relative to a longitudinal axis of the shaft, from the hinge.

* * * * *